US005885813A

United States Patent [19]
Davis et al.

[11] Patent Number: 5,885,813
[45] Date of Patent: Mar. 23, 1999

[54] THERMOSTABLE DNA POLYMERASES

[75] Inventors: Maria Davis, Twinsburg; R. Bruce Moffett, Shaker Heights; Carl W. Fuller, Cleveland Heights; John J. Cunniff, Akron, all of Ohio

[73] Assignee: Amersham Life Science, Inc., Cleveland, Ohio

[21] Appl. No.: 648,657

[22] Filed: May 14, 1996

Related U.S. Application Data

[63] Continuation-in-part of Ser. No. 455,686, May 31, 1995, abandoned.

[51] Int. Cl.⁶ .............................. C12N 9/00; C12N 9/12; C12N 19/34
[52] U.S. Cl. .................. 435/183; 435/194; 435/91.1; 435/91.2
[58] Field of Search .................. 435/183, 194, 435/810, 91.1, 91.2

[56] References Cited

U.S. PATENT DOCUMENTS

| | | |
|---|---|---|
| 4,795,699 | 1/1989 | Tabor et al. |
| 4,889,818 | 12/1989 | Gelfand et al. |
| 5,075,216 | 12/1991 | Innis et al. |
| 5,079,352 | 1/1992 | Gelfand et al. |
| 5,436,149 | 7/1995 | Barnes ..................... 435/194 |
| 5,466,591 | 11/1995 | Abramson et al. ............. 435/194 |
| 5,474,920 | 12/1995 | Moses ..................... 435/194 |

FOREIGN PATENT DOCUMENTS

| | | |
|---|---|---|
| 0655506 | 5/1995 | European Pat. Off. |
| 9206188 | 4/1990 | WIPO. |
| 9012111 | 10/1990 | WIPO. |
| 9109944 | 7/1991 | WIPO. |
| WO92/06200 | 4/1992 | WIPO ..................... C12N 15/54 |
| 9405797 | 3/1994 | WIPO. |

OTHER PUBLICATIONS

Barnes, "The fidelity of *Taq* polymerase catalizing PCR is improved by an N–terminal deletion," *Gene* 112;29–35 (1992).

Reeve and Fuller, "A novel thermostable polymerase for DNA sequencing," *Nature* 376:796–797 (1995).

Samols et al., "Thermo Sequenase; a new thermostable DNA polymerase for DNA sequencing," *Amersham Life Science, Editorial Comments* 22:29–36 (1995).

Tabor and Richardson, "A single residue in DNA polymerases of the *Escherichia coli* DNA polymerase 1 family is critical for distinguishing between deoxy and dideoxyribonucleotides," *Proc. Natl. Acad. Sci. USA* 92:6339–6343 (1995).

Phang et al. (1995) Gene 163:65–68.
Gutman et al. (1993) J. Bacteriol. 175:3581–3590.
Asakura et al. (1993) J. Frement. Bioengin. 76:265–269.
Lawyer et al. (1989) J. Biol. Chem. 264:6427–6437.
Akhmetzjanov et al. (1992) Nucl. Acids Res. 20:5839.
Kim et al. (1995) Nature 376:612–616.

*Primary Examiner*—Ardin H. Marschel
*Assistant Examiner*—Jezia Riley
*Attorney, Agent, or Firm*—Lyon & Lyon LLP

[57] ABSTRACT

An enzymatically active DNA polymerase having between 540 and 582 amino acids having a tyrosine at a position equivalent to position 667 of Taq DNA polymerase, wherein said polymerase lacks 5' to 3' exonuclease activity, and wherein said polymerase has at least 95% homology in its amino acid sequence to the DNA polymerase of *Thermus aquaticus, Thermus flavus* or *Thermus thermophilus,* and wherein said polymerase forms a single polypeptide band on an SDS PAGE.

22 Claims, 12 Drawing Sheets

Fig. 1A

```
1081/361                                                                              1111/371                              1141/381
ttc cag gag ggg cgg gac atc cac acg gag acc gcc agc tgg atg ttc ggc gtc ccc cgg gag gcc gtg gac ccc ctg atg cgc cgg gcg
 F   Q   E   G   R   D   I   H   T   E   T   A   S   W   M   F   G   V   P   R   E   A   V   D   P   L   M   R   R   A
1171/391                                                                              1201/401                             1231/411
gcc aag acc atc aac tac ggg gtc ctc tac ggc atg tcg gcc cac cgc ctc tcc cag gag cta gcc atc cct tac gag gag gcc cag gcc
 A   K   T   I   N   Y   G   V   L   Y   G   M   S   A   H   R   L   S   Q   E   L   A   I   P   Y   E   E   A   Q   A
1261/421                                                                              1291/431                             1321/441
ttc att gag cgc tac ttt cag agc ttc ccc aag gtg cgg gcc tgg att gag aag acc ctg gag gag ggc agg agg cgg atg gga tac gtg gag
 F   I   E   R   Y   F   Q   S   F   P   K   V   R   A   W   I   E   K   T   L   E   E   G   R   R   R   M   G   Y   V   E
1351/451                                                                              1381/461                             1411/471
acc ctc ttc ggc cgc cgc tac gac cta gag gcc cgg gtg aag agc gtg cgg gag gcg gcc gag cgc atg gcc ttc aac atg
 T   L   F   G   R   R   Y   D   L   E   A   R   V   K   S   V   R   E   A   A   E   R   M   A   F   N   M
1441/481                                                                              1471/491                             1501/501
ccc gtc cag ggc acc gcc gac ctc atg aag ctg gct atg gtg aag ctc ttc ccc agg ctg gag gaa atg ggg gcc agg atg ctc ctt
 P   V   Q   G   T   A   D   L   M   K   L   A   M   V   K   L   F   P   R   L   E   E   M   G   A   R   M   L   L
1531/511                                                                              1561/521                             1591/531
cag gtc cac gac gag ctg gtc ctc gag gcc cca aaa gag agg gcg gcc gtg gcc aag gag gcg aag gag gtc atg gag ggg gtg tat
 Q   V   H   D   E   L   V   L   E   A   P   K   E   R   A   A   V   A   K   E   A   K   E   V   M   E   G   V   Y
1621/541                                                                              1651/551                             1681/561
ccc ctg gcc gtg ccc ctg gag gtg gtg ggg ata ggg gag gac tgg ctc tcc gcc aag gag tga
 P   L   A   V   P   L   E   V   V   G   I   G   E   D   W   L   S   A   K   E   *
```

```
1081/361
gtc ttc cag gag ggg cgg gac atc cac acg gag acc gcc agc tgg atg ttc ggc gtc ccc   1141/381
 V   F   Q   E   G   R   D   I   H   T   E   T   A   S   W   M   F   G   V   P    cgg gag gcc gtg gac ccc ctg atg cgc cgg
1171/391                                                                            R   E   A   V   D   P   L   M   R   R
gcg gcc aag acc atc aac tac ggg gtc ctc tac ggc atg tcg gcc cac cgc ctc tcc cag   1231/411
 A   A   K   T   I   N   Y   G   V   L   Y   G   M   S   A   H   R   L   S   Q    gag cta gcc atc cct tac gag gag gcc cag
1261/421                                                                            E   L   A   I   P   Y   E   E   A   Q
gcc ttc att gag cgc tac ttt cag agc ttc ccc aag gtg cgg gcc tgg att gag aag acc   1321/441
 A   F   I   E   R   Y   F   Q   S   F   P   K   V   R   A   W   I   E   K   T    ctg gag gag ggc agg agg cgg ggg tac gtg
1351/451                                                                            L   E   E   G   R   R   R   G   Y   V
gag acc ctc ttc ggc cgc cgc cgc tac gtg cca gac cta gag gcc cgg gtg aag agc gtg   1411/471
 E   T   L   F   G   R   R   R   Y   V   P   D   L   E   A   R   V   K   S   V    cgg gag gcg gcc atg cgc atg gcc ttc aac
1441/481                                                                            R   E   A   A   M   R   M   A   F   N
atg ccc gtc cag ggc acc gcc gcc gac ctc atg aag ctg gct atg gtg aag ctc ttc ccc   1501/501
 M   P   V   Q   G   T   A   A   D   L   M   K   L   A   M   V   K   L   F   P    agg ctg gag gaa atg ggg gcc agg atg ctc
1531/511                                                                            R   L   E   E   M   G   A   R   M   L
ctt cag gtc cac gac gag gag ctg gtc ctc gag gcc cca aaa gag agg gcg gag gcc gtg   1591/531
 L   Q   V   H   D   E   E   L   V   L   E   A   P   K   E   R   A   E   A   V    cgg ctg gcc aag gag gtg atg gag ggg gtg
1621/541                                                                            R   L   A   K   E   V   M   E   G   V
tat ccc ctg gcc gtg ccc ctg gag gtg gag gtg ggg ata ggg gag gac tgg ctc tcc gcc   1681/561
 Y   P   L   A   V   P   L   E   V   E   V   G   I   G   E   D   W   L   S   A    aag gag tga
1651/551                                                                            K   E   *
```

```
2161/721
acc ctc ttc ggc cgc cgg cgc tat gtg ccc        2191/731
 T   L   F   G   R   R   R   Y   V   P   gac ctc aac gcc cgg gtg aag agc gtg cgc        2221/741
                                          D   L   N   A   R   V   K   S   V   R   gag gcg gcg gag cgc atg gcc ttc aac atg
2251/751                                                                                  E   A   A   E   R   M   A   F   N   M
ccg gtc cag ggc acc gcc gac ctc atg        2281/761
 P   V   Q   G   T   A   D   L   M   aag ctg gcc atg gtg cgg ctt ttc ccc cgg        2311/771
                                        K   L   A   M   V   R   L   F   P   R   ctt cag gaa ctg ggg gcg agg atg ctt ttg
2341/781                                                                                  L   Q   E   L   G   A   R   M   L   L
cag gtg cac gac gag ctg gtc ctc gag gcc        2371/791
 Q   V   H   D   E   L   V   L   E   A   ccc aag gac cgg gag agg gta gcc gct        2401/801
                                          P   K   D   R   E   R   V   A   A   ttg gcc aag gag ggg gtc atg gag ggg tgg
2431/811                                                                                  L   A   K   E   M   E   G   V   W
ccc ctg cag gtg ccc ctg gag gtg ggg ggc        2461/821
 P   L   Q   V   P   L   E   V   G   G   ctg gag gac tgg ctc tcc gcc aag        2491/831
                                          L   E   D   W   L   S   A   K   gag tag
                                                                                          E   *
```

```
2161/721
TAC GTG GAA ACC CTC TTC GGA AGA AGG CGC TAC GTG CCC GAC CTC AAC GCC CGG GTG AAG AGC GTC AGG GAG GCC GCG GAG CGC ATG GCC
 Y   V   E   T   L   F   G   R   R   R   Y   V   P   D   L   N   A   R   V   K   S   V   R   E   A   A   E   R   M   A
                                                   2191/731                            2221/741
2251/751                                    2281/761
TTC AAC ATG CCC GTC CAG GGC ACC GCC GCC ATG GAC CTC ATG AAG CTC GCC ATG GTG AAG CTC TTC CCC CGC CTC CGG GAG ATG GGG GCC CGC
 F   N   M   P   V   Q   G   T   A   A   M   D   L   M   K   L   A   M   V   K   L   F   P   R   L   R   E   M   G   A   R
                                                                                       2311/771
2341/781                                    2371/791
ATG CTC CTC CAG GTC CAC GAC GAG CTC CTC CTG GAG CTC CTC CCC CAA GCG CGG GAG GAG GAG GTG GCG GCT TTG GCC AAG GAG GCC ATG GAG
 M   L   L   Q   V   H   D   E   L   L   L   E   L   L   P   Q   A   R   E   E   E   V   A   A   L   A   K   E   A   M   E
                                  2401/801
2431/811                    2461/821                2491/831
AAG GCC TAT CCC CTC GCC GTG CCC CTG GAG GTG GAG GTG GGG ATG GGG GAG GAG GAC TGG CTT TCC GCC AAG GGT TAG
 K   A   Y   P   L   A   V   P   L   E   V   E   V   G   M   G   E   E   D   W   L   S   A   K   G   *
```

```
1081/361
TTC CAG GAG GGG AAG GAC ATC CAC ACC CAG AGC TGG ATG TTC GGC GTC CCC CCG
 F   Q   E   G   K   D   I   H   T   Q   S   W   M   F   G   V   P   P
1111/371                                            1141/381
                                                    GAG GCC GTG GAC CCC CTG ATG CGC CGG GCG
                                                     E   A   V   D   P   L   M   R   R   A
1171/391
GCC AAG ACG GTG AAC TAC GGC GTC CTC TAC CCC CAT AGG CTC TCC CAG GAG
 A   K   T   V   N   Y   G   V   L   Y   P   H   R   L   S   Q   E
1201/401                                            1231/411
                                                    CTA GCC ATC GCC TAC GAA GAA GCG GTG GCC
                                                     L   A   I   A   Y   E   E   A   V   A
1261/421
TTT ATA GAG CGC TAC TTC CAA AGC TTC CCC AAG GTG CGG GCC ACC CTG
 F   I   E   R   Y   F   Q   S   F   P   K   V   R   A   T   L
1291/431                                            1321/441
                                                    GAG GAG GGG AGG AAG TAC GTG GAA
                                                     E   E   G   R   K   Y   V   E
1351/451
ACC CTC TTC GGA AGA AGG CGC TAC GTG CCC GAC CTC AAC GCC CGG GTG AAG AGC GTC AGG
 T   L   F   G   R   R   R   Y   V   P   D   L   N   A   R   V   K   S   V   R
1381/461                                            1411/471
                                                    GAG GCC GCG ATG GCC TTC
                                                     E   A   A   M   A   F
1441/481
CCC GTC CAG ACC GCC GCC CTC GCC ATG AAG CTC GCC ATG GTG CGG GCC GAG GAG
 P   V   Q   T   A   A   L   A   M   K   L   A   M   V   R   A   E   E
1471/491                                            1501/501
                                                    CTC CGG GAG CGC ATG CTC CTC
                                                     L   R   E   R   M   L   L
1531/511
CAG GTC CAC GAG GAC CTC CTC CTG GAG GTG CCC CAA GCG GCC GGG GAG GTG GCG GCT
 Q   V   H   E   D   L   L   L   E   V   P   Q   A   A   G   E   V   A   A
1561/521                                            1591/531
                                                    TTG GCC AAG GAG ATG GAG AAG GCC TAT
                                                     L   A   K   E   M   E   K   A   Y
1621/541
CCC CTC GCC CTG CCC GTG GAG GAG GTG GGG GAG ATG GGG GAG GAC TGG CTT TCC GCC
 P   L   A   L   P   V   E   E   V   G   E   M   G   E   D   W   L   S   A
1651/551                                            1681/561
                                                    AAG GGT TAG
                                                     K   G   *
```

Fig. 5B

SEQUENCE LISTING ( 1 ) GENERAL INFORMATION:

( i i i ) NUMBER OF SEQUENCES: 14

( 2 ) INFORMATION FOR SEQ ID NO: 1:

( i ) SEQUENCE CHARACTERISTICS:
( A ) LENGTH: 1686 base pairs
( B ) TYPE: nucleic acid
( C ) STRANDEDNESS: single
( D ) TOPOLOGY: linear ( i x ) FEATURE:
( A ) NAME/KEY: FY2
( B ) LOCATION: 1...1683

( x i ) SEQUENCE DESCRIPTION: SEQ ID NO: 1:

```
ATG  CTG  GAG  AGG  CTT  GAG  TTT  GGC  AGC  CTC  CTC  CAC  GAG  TTC  GGC  CTT         48
Met  Leu  Glu  Arg  Leu  Glu  Phe  Gly  Ser  Leu  Leu  His  Glu  Phe  Gly  Leu
 1                   5                        10                      15

CTG  GAA  AGC  CCC  AAG  GCC  CTG  GAG  GAG  GCC  CCC  TGG  CCC  CCG  CCG  GAA         96
Leu  Glu  Ser  Pro  Lys  Ala  Leu  Glu  Glu  Ala  Pro  Trp  Pro  Pro  Pro  Glu
                20                       25                      30

GGG  GCC  TTC  GTG  GGC  TTT  GTG  CTT  TCC  CGC  AAG  GAG  CCC  ATG  TGG  GCC        144
Gly  Ala  Phe  Val  Gly  Phe  Val  Leu  Ser  Arg  Lys  Glu  Pro  Met  Trp  Ala
           35                        40                      45

GAT  CTT  CTG  GCC  CTG  GCC  GCC  GCC  AGG  GGG  GGC  CGG  GTC  CAC  CGG  GCC        192
Asp  Leu  Leu  Ala  Leu  Ala  Ala  Ala  Arg  Gly  Gly  Arg  Val  His  Arg  Ala
     50                        55                      60

CCC  GAG  CCT  TAT  AAA  GCC  CTC  AGG  GAC  CTG  AAG  GAG  GCG  CGG  GGG  CTT        240
Pro  Glu  Pro  Tyr  Lys  Ala  Leu  Arg  Asp  Leu  Lys  Glu  Ala  Arg  Gly  Leu
65                       70                      75                      80

CTC  GCC  AAA  GAC  CTG  AGC  GTT  CTG  GCC  CTG  AGG  GAA  GGC  CTT  GGC  CTC        288
Leu  Ala  Lys  Asp  Leu  Ser  Val  Leu  Ala  Leu  Arg  Glu  Gly  Leu  Gly  Leu
                     85                       90                      95

CCG  CCC  GGC  GAC  GAC  CCC  ATG  CTC  CTC  GCC  TAC  CTC  CTG  GAC  CCT  TCC        336
Pro  Pro  Gly  Asp  Asp  Pro  Met  Leu  Leu  Ala  Tyr  Leu  Leu  Asp  Pro  Ser
              100                      105                     110

AAC  ACC  ACC  CCC  GAG  GGG  GTG  GCC  CGG  CGC  TAC  GGC  GGG  GAG  TGG  ACG        384
Asn  Thr  Thr  Pro  Glu  Gly  Val  Ala  Arg  Arg  Tyr  Gly  Gly  Glu  Trp  Thr
         115                      120                     125

GAG  GAG  GCG  GGG  GAG  CGG  GCC  GCC  CTT  TCC  GAG  AGG  CTC  TTC  GCC  AAC        432
Glu  Glu  Ala  Gly  Glu  Arg  Ala  Ala  Leu  Ser  Glu  Arg  Leu  Phe  Ala  Asn
    130                      135                     140
```

```
CTG  TGG  GGG  AGG  CTT  GAG  GGG  GAG  GAG  AGG  CTC  CTT  TGG  CTT  TAC  CGG       480
Leu  Trp  Gly  Arg  Leu  Glu  Gly  Glu  Glu  Arg  Leu  Leu  Trp  Leu  Tyr  Arg
145            150                           155                           160

GAG  GTG  GAG  AGG  CCC  CTT  TCC  GCT  GTC  CTG  GCC  CAC  ATG  GAG  GCC  ACG       528
Glu  Val  Glu  Arg  Pro  Leu  Ser  Ala  Val  Leu  Ala  His  Met  Glu  Ala  Thr
                165                           170                           175

GGG  GTG  CGC  CTG  GAC  GTG  GCC  TAT  CTC  AGG  GCC  TTG  TCC  CTG  GAG  GTG       576
Gly  Val  Arg  Leu  Asp  Val  Ala  Tyr  Leu  Arg  Ala  Leu  Ser  Leu  Glu  Val
                    180                           185                      190

GCC  GAG  GAG  ATC  GCC  CGC  CTC  GAG  GCC  GAG  GTC  TTC  CGC  CTG  GCC  GGC       624
Ala  Glu  Glu  Ile  Ala  Arg  Leu  Glu  Ala  Glu  Val  Phe  Arg  Leu  Ala  Gly
               195                           200                          205

CAC  CCC  TTC  AAC  CTC  AAC  TCC  CGG  GAC  CAG  CTG  GAA  AGG  GTC  CTC  TTT       672
His  Pro  Phe  Asn  Leu  Asn  Ser  Arg  Asp  Gln  Leu  Glu  Arg  Val  Leu  Phe
          210                           215                      220

GAC  GAG  CTA  GGG  CTT  CCC  GCC  ATC  GGC  AAG  ACG  GAG  AAG  ACC  GGC  AAG       720
Asp  Glu  Leu  Gly  Leu  Pro  Ala  Ile  Gly  Lys  Thr  Glu  Lys  Thr  Gly  Lys
225                      230                      235                      240

CGC  TCC  ACC  AGC  GCC  GCC  GTC  CTG  GAG  GCC  CTC  CGC  GAG  GCC  CAC  CCC       768
Arg  Ser  Thr  Ser  Ala  Ala  Val  Leu  Glu  Ala  Leu  Arg  Glu  Ala  His  Pro
                    245                           250                      255

ATC  GTG  GAG  AAG  ATC  CTG  CAG  TAC  CGG  GAG  CTC  ACC  AAG  CTG  AAG  AGC       816
Ile  Val  Glu  Lys  Ile  Leu  Gln  Tyr  Arg  Glu  Leu  Thr  Lys  Leu  Lys  Ser
               260                           265                      270

ACC  TAC  ATT  GAC  CCC  TTG  CCG  GAC  CTC  ATC  CAC  CCC  AGG  ACG  GGC  CGC       864
Thr  Tyr  Ile  Asp  Pro  Leu  Pro  Asp  Leu  Ile  His  Pro  Arg  Thr  Gly  Arg
               275                           280                      285

CTC  CAC  ACC  CGC  TTC  AAC  CAG  ACG  GCC  ACG  GCC  ACG  GGC  AGG  CTA  AGT       912
Leu  His  Thr  Arg  Phe  Asn  Gln  Thr  Ala  Thr  Ala  Thr  Gly  Arg  Leu  Ser
     290                           295                      300

AGC  TCC  GAT  CCC  AAC  CTC  CAG  AAC  ATC  CCC  GTC  CGC  ACC  CCG  CTT  GGG       960
Ser  Ser  Asp  Pro  Asn  Leu  Gln  Asn  Ile  Pro  Val  Arg  Thr  Pro  Leu  Gly
305                      310                      315                      320

CAG  AGG  ATC  CGC  CGG  GCC  TTC  ATC  GCC  GAG  GAG  GGG  TGG  CTA  TTG  GTG      1008
Gln  Arg  Ile  Arg  Arg  Ala  Phe  Ile  Ala  Glu  Glu  Gly  Trp  Leu  Leu  Val
               325                           330                      335

GCC  CTG  GAC  TAT  AGC  CAG  ATA  GAG  CTC  AGG  GTG  CTG  GCC  CAC  CTC  TCC      1056
Ala  Leu  Asp  Tyr  Ser  Gln  Ile  Glu  Leu  Arg  Val  Leu  Ala  His  Leu  Ser
               340                           345                      350

GGC  GAC  GAG  AAC  CTG  ATC  CGG  GTC  TTC  CAG  GAG  GGG  CGG  GAC  ATC  CAC      1104
Gly  Asp  Glu  Asn  Leu  Ile  Arg  Val  Phe  Gln  Glu  Gly  Arg  Asp  Ile  His
          355                           360                      365

ACG  GAG  ACC  GCC  AGC  TGG  ATG  TTC  GGC  GTC  CCC  CGG  GAG  GCC  GTG  GAC      1152
Thr  Glu  Thr  Ala  Ser  Trp  Met  Phe  Gly  Val  Pro  Arg  Glu  Ala  Val  Asp
     370                           375                      380

CCC  CTG  ATG  CGC  CGG  GCG  GCC  AAG  ACC  ATC  AAC  TAC  GGG  GTC  CTC  TAC      1200
Pro  Leu  Met  Arg  Arg  Ala  Ala  Lys  Thr  Ile  Asn  Tyr  Gly  Val  Leu  Tyr
385                      390                      395                      400

GGC  ATG  TCG  GCC  CAC  CGC  CTC  TCC  CAG  GAG  CTA  GCC  ATC  CCT  TAC  GAG      1248
Gly  Met  Ser  Ala  His  Arg  Leu  Ser  Gln  Glu  Leu  Ala  Ile  Pro  Tyr  Glu
               405                           410                      415

GAG  GCC  CAG  GCC  TTC  ATT  GAG  CGC  TAC  TTT  CAG  AGC  TTC  CCC  AAG  GTG      1296
Glu  Ala  Gln  Ala  Phe  Ile  Glu  Arg  Tyr  Phe  Gln  Ser  Phe  Pro  Lys  Val
               420                           425                      430

CGG  GCC  TGG  ATT  GAG  AAG  ACC  CTG  GAG  GAG  GGC  AGG  AGG  CGG  GGG  TAC      1344
Arg  Ala  Trp  Ile  Glu  Lys  Thr  Leu  Glu  Glu  Gly  Arg  Arg  Arg  Gly  Tyr
               435                           440                      445

GTG  GAG  ACC  CTC  TTC  GGC  CGC  CGC  CGC  TAC  GTG  CCA  GAC  CTA  GAG  GCC      1392
Val  Glu  Thr  Leu  Phe  Gly  Arg  Arg  Arg  Tyr  Val  Pro  Asp  Leu  Glu  Ala
     450                           455                      460
```

```
CGG  GTG  AAG  AGC  GTG  CGG  GAG  GCG  GCC  GAG  CGC  ATG  GCC  TTC  AAC  ATG    1440
Arg  Val  Lys  Ser  Val  Arg  Glu  Ala  Ala  Glu  Arg  Met  Ala  Phe  Asn  Met
465                      470                      475                      480

CCC  GTC  CAG  GGC  ACC  GCC  GCC  GAC  CTC  ATG  AAG  CTG  GCT  ATG  GTG  AAG    1488
Pro  Val  Gln  Gly  Thr  Ala  Ala  Asp  Leu  Met  Lys  Leu  Ala  Met  Val  Lys
                    485                      490                      495

CTC  TTC  CCC  AGG  CTG  GAG  GAA  ATG  GGG  GCC  AGG  ATG  CTC  CTT  CAG  GTC    1536
Leu  Phe  Pro  Arg  Leu  Glu  Glu  Met  Gly  Ala  Arg  Met  Leu  Leu  Gln  Val
               500                      505                      510

CAC  GAC  GAG  CTG  GTC  CTC  GAG  GCC  CCA  AAA  GAG  AGG  GCG  GAG  GCC  GTG    1584
His  Asp  Glu  Leu  Val  Leu  Glu  Ala  Pro  Lys  Glu  Arg  Ala  Glu  Ala  Val
          515                      520                      525

GCC  CGG  CTG  GCC  AAG  GAG  GTC  ATG  GAG  GGG  GTG  TAT  CCC  CTG  GCC  GTG    1632
Ala  Arg  Leu  Ala  Lys  Glu  Val  Met  Glu  Gly  Val  Tyr  Pro  Leu  Ala  Val
     530                      535                      540

CCC  CTG  GAG  GTG  GAG  GTG  GGG  ATA  GGG  GAG  GAC  TGG  CTC  TCC  GCC  AAG    1680
Pro  Leu  Glu  Val  Glu  Val  Gly  Ile  Gly  Glu  Asp  Trp  Leu  Ser  Ala  Lys
545                      550                      555                      560

GAG  TGA                                                                          1686
Glu  *
```

( 2 ) INFORMATION FOR SEQ ID NO: 2:

( i ) SEQUENCE CHARACTERISTICS:
( A ) LENGTH: 1689 base pairs
( B ) TYPE: nucleic acid
( C ) STRANDEDNESS: single
( D ) TOPOLOGY: linear ( i x ) FEATURE:
( A ) NAME/KEY: FY3
( B ) LOCATION: 1...1686

( x i ) SEQUENCE DESCRIPTION: SEQ ID NO: 2:

```
ATG  GCT  CTG  GAA  CGT  CTG  GAG  TTT  GGC  AGC  CTC  CTC  CAC  GAG  TTC  GGC      48
Met  Ala  Leu  Glu  Arg  Leu  Glu  Phe  Gly  Ser  Leu  Leu  His  Glu  Phe  Gly
1                   5                        10                       15

CTT  CTG  GAA  AGC  CCC  AAG  GCC  CTG  GAG  GAG  GCC  CCC  TGG  CCC  CCG  CCG      96
Leu  Leu  Glu  Ser  Pro  Lys  Ala  Leu  Glu  Glu  Ala  Pro  Trp  Pro  Pro  Pro
                    20                       25                       30

GAA  GGG  GCC  TTC  GTG  GGC  TTT  GTG  CTT  TCC  CGC  AAG  GAG  CCC  ATG  TGG     144
Glu  Gly  Ala  Phe  Val  Gly  Phe  Val  Leu  Ser  Arg  Lys  Glu  Pro  Met  Trp
          35                       40                       45

GCC  GAT  CTT  CTG  GCC  CTG  GCC  GCC  AGG  GGG  GGC  CGG  GTC  CAC  CGG         192
Ala  Asp  Leu  Leu  Ala  Leu  Ala  Ala  Arg  Gly  Gly  Arg  Val  His  Arg
     50                       55                       60

GCC  CCC  GAG  CCT  TAT  AAA  GCC  CTC  AGG  GAC  CTG  AAG  GAG  GCG  CGG  GGG     240
Ala  Pro  Glu  Pro  Tyr  Lys  Ala  Leu  Arg  Asp  Leu  Lys  Glu  Ala  Arg  Gly
65                       70                       75                       80

CTT  CTC  GCC  AAA  GAC  CTG  AGC  GTT  CTG  GCC  CTG  AGG  GAA  GGC  CTT  GGC     288
Leu  Leu  Ala  Lys  Asp  Leu  Ser  Val  Leu  Ala  Leu  Arg  Glu  Gly  Leu  Gly
               85                       90                       95

CTC  CCG  CCC  GGC  GAC  GAC  CCC  ATG  CTC  CTC  GCC  TAC  CTC  CTG  GAC  CCT     336
Leu  Pro  Pro  Gly  Asp  Asp  Pro  Met  Leu  Leu  Ala  Tyr  Leu  Leu  Asp  Pro
               100                      105                      110

TCC  AAC  ACC  ACC  CCC  GAG  GGG  GTG  GCC  CGG  CGC  TAC  GGC  GGG  GAG  TGG     384
Ser  Asn  Thr  Thr  Pro  Glu  Gly  Val  Ala  Arg  Arg  Tyr  Gly  Gly  Glu  Trp
               115                      120                      125

ACG  GAG  GAG  GCG  GGG  GAG  CGG  GCC  GCC  CTT  TCC  GAG  AGG  CTC  TTC  GCC     432
Thr  Glu  Glu  Ala  Gly  Glu  Arg  Ala  Ala  Leu  Ser  Glu  Arg  Leu  Phe  Ala
          130                      135                      140

AAC  CTG  TGG  GGG  AGG  CTT  GAG  GGG  GAG  GAG  AGG  CTC  CTT  TGG  CTT  TAC     480
```

-continued

| Asn | Leu | Trp | Gly | Arg | Leu | Glu | Gly | Glu | Glu | Arg | Leu | Leu | Trp | Leu | Tyr | |
|---|---|---|---|---|---|---|---|---|---|---|---|---|---|---|---|---|
| 145 | | | | 150 | | | | | 155 | | | | | | 160 | |

| CGG | GAG | GTG | GAG | AGG | CCC | CTT | TCC | GCT | GTC | CTG | GCC | CAC | ATG | GAG | GCC | 528 |
|---|---|---|---|---|---|---|---|---|---|---|---|---|---|---|---|---|
| Arg | Glu | Val | Glu | Arg | Pro | Leu | Ser | Ala | Val | Leu | Ala | His | Met | Glu | Ala | |
| | | | | 165 | | | | | 170 | | | | | 175 | | |

| ACG | GGG | GTG | CGC | CTG | GAC | GTG | GCC | TAT | CTC | AGG | GCC | TTG | TCC | CTG | GAG | 576 |
|---|---|---|---|---|---|---|---|---|---|---|---|---|---|---|---|---|
| Thr | Gly | Val | Arg | Leu | Asp | Val | Ala | Tyr | Leu | Arg | Ala | Leu | Ser | Leu | Glu | |
| | | | 180 | | | | | 185 | | | | | 190 | | | |

| GTG | GCC | GAG | GAG | ATC | GCC | CGC | CTC | GAG | GCC | GAG | GTC | TTC | CGC | CTG | GCC | 624 |
|---|---|---|---|---|---|---|---|---|---|---|---|---|---|---|---|---|
| Val | Ala | Glu | Glu | Ile | Ala | Arg | Leu | Glu | Ala | Glu | Val | Phe | Arg | Leu | Ala | |
| | | 195 | | | | | 200 | | | | | 205 | | | | |

| GGC | CAC | CCC | TTC | AAC | CTC | AAC | TCC | CGG | GAC | CAG | CTG | GAA | AGG | GTC | CTC | 672 |
|---|---|---|---|---|---|---|---|---|---|---|---|---|---|---|---|---|
| Gly | His | Pro | Phe | Asn | Leu | Asn | Ser | Arg | Asp | Gln | Leu | Glu | Arg | Val | Leu | |
| | 210 | | | | | 215 | | | | | 220 | | | | | |

| TTT | GAC | GAG | CTA | GGG | CTT | CCC | GCC | ATC | GGC | AAG | ACG | GAG | AAG | ACC | GGC | 720 |
|---|---|---|---|---|---|---|---|---|---|---|---|---|---|---|---|---|
| Phe | Asp | Glu | Leu | Gly | Leu | Pro | Ala | Ile | Gly | Lys | Thr | Glu | Lys | Thr | Gly | |
| 225 | | | | | 230 | | | | | 235 | | | | | 240 | |

| AAG | CGC | TCC | ACC | AGC | GCC | GCC | GTC | CTG | GAG | GCC | CTC | CGC | GAG | GCC | CAC | 768 |
|---|---|---|---|---|---|---|---|---|---|---|---|---|---|---|---|---|
| Lys | Arg | Ser | Thr | Ser | Ala | Ala | Val | Leu | Glu | Ala | Leu | Arg | Glu | Ala | His | |
| | | | | 245 | | | | | 250 | | | | | 255 | | |

| CCC | ATC | GTG | GAG | AAG | ATC | CTG | CAG | TAC | CGG | GAG | CTC | ACC | AAG | CTG | AAG | 816 |
|---|---|---|---|---|---|---|---|---|---|---|---|---|---|---|---|---|
| Pro | Ile | Val | Glu | Lys | Ile | Leu | Gln | Tyr | Arg | Glu | Leu | Thr | Lys | Leu | Lys | |
| | | | 260 | | | | | 265 | | | | | 270 | | | |

| AGC | ACC | TAC | ATT | GAC | CCC | TTG | CCG | GAC | CTC | ATC | CAC | CCC | AGG | ACG | GGC | 864 |
|---|---|---|---|---|---|---|---|---|---|---|---|---|---|---|---|---|
| Ser | Thr | Tyr | Ile | Asp | Pro | Leu | Pro | Asp | Leu | Ile | His | Pro | Arg | Thr | Gly | |
| | | 275 | | | | | 280 | | | | | 285 | | | | |

| CGC | CTC | CAC | ACC | CGC | TTC | AAC | CAG | ACG | GCC | ACG | GCC | ACG | GGC | AGG | CTA | 912 |
|---|---|---|---|---|---|---|---|---|---|---|---|---|---|---|---|---|
| Arg | Leu | His | Thr | Arg | Phe | Asn | Gln | Thr | Ala | Thr | Ala | Thr | Gly | Arg | Leu | |
| | 290 | | | | | 295 | | | | | 300 | | | | | |

| AGT | AGC | TCC | GAT | CCC | AAC | CTC | CAG | AAC | ATC | CCC | GTC | CGC | ACC | CCG | CTT | 960 |
|---|---|---|---|---|---|---|---|---|---|---|---|---|---|---|---|---|
| Ser | Ser | Ser | Asp | Pro | Asn | Leu | Gln | Asn | Ile | Pro | Val | Arg | Thr | Pro | Leu | |
| 305 | | | | | 310 | | | | | 315 | | | | | 320 | |

| GGG | CAG | AGG | ATC | CGC | CGG | GCC | TTC | ATC | GCC | GAG | GAG | GGG | TGG | CTA | TTG | 1008 |
|---|---|---|---|---|---|---|---|---|---|---|---|---|---|---|---|---|
| Gly | Gln | Arg | Ile | Arg | Arg | Ala | Phe | Ile | Ala | Glu | Glu | Gly | Trp | Leu | Leu | |
| | | | | 325 | | | | | 330 | | | | | 335 | | |

| GTG | GCC | CTG | GAC | TAT | AGC | CAG | ATA | GAG | CTC | AGG | GTG | CTG | GCC | CAC | CTC | 1056 |
|---|---|---|---|---|---|---|---|---|---|---|---|---|---|---|---|---|
| Val | Ala | Leu | Asp | Tyr | Ser | Gln | Ile | Glu | Leu | Arg | Val | Leu | Ala | His | Leu | |
| | | | 340 | | | | | 345 | | | | | 350 | | | |

| TCC | GGC | GAC | GAG | AAC | CTG | ATC | CGG | GTC | TTC | CAG | GAG | GGG | CGG | GAC | ATC | 1104 |
|---|---|---|---|---|---|---|---|---|---|---|---|---|---|---|---|---|
| Ser | Gly | Asp | Glu | Asn | Leu | Ile | Arg | Val | Phe | Gln | Glu | Gly | Arg | Asp | Ile | |
| | | 355 | | | | | 360 | | | | | 365 | | | | |

| CAC | ACG | GAG | ACC | GCC | AGC | TGG | ATG | TTC | GGC | GTC | CCC | CGG | GAG | GCC | GTG | 1152 |
|---|---|---|---|---|---|---|---|---|---|---|---|---|---|---|---|---|
| His | Thr | Glu | Thr | Ala | Ser | Trp | Met | Phe | Gly | Val | Pro | Arg | Glu | Ala | Val | |
| | 370 | | | | | 375 | | | | | 380 | | | | | |

| GAC | CCC | CTG | ATG | CGC | CGG | GCG | GCC | AAG | ACC | ATC | AAC | TAC | GGG | GTC | CTC | 1200 |
|---|---|---|---|---|---|---|---|---|---|---|---|---|---|---|---|---|
| Asp | Pro | Leu | Met | Arg | Arg | Ala | Ala | Lys | Thr | Ile | Asn | Tyr | Gly | Val | Leu | |
| 385 | | | | | 390 | | | | | 395 | | | | | 400 | |

| TAC | GGC | ATG | TCG | GCC | CAC | CGC | CTC | TCC | CAG | GAG | CTA | GCC | ATC | CCT | TAC | 1248 |
|---|---|---|---|---|---|---|---|---|---|---|---|---|---|---|---|---|
| Tyr | Gly | Met | Ser | Ala | His | Arg | Leu | Ser | Gln | Glu | Leu | Ala | Ile | Pro | Tyr | |
| | | | | 405 | | | | | 410 | | | | | 415 | | |

| GAG | GAG | GCC | CAG | GCC | TTC | ATT | GAG | CGC | TAC | TTT | CAG | AGC | TTC | CCC | AAG | 1296 |
|---|---|---|---|---|---|---|---|---|---|---|---|---|---|---|---|---|
| Glu | Glu | Ala | Gln | Ala | Phe | Ile | Glu | Arg | Tyr | Phe | Gln | Ser | Phe | Pro | Lys | |
| | | | | 420 | | | | | 425 | | | | | 430 | | |

| GTG | CGG | GCC | TGG | ATT | GAG | AAG | ACC | CTG | GAG | GAG | GGC | AGG | AGG | CGG | GGG | 1344 |
|---|---|---|---|---|---|---|---|---|---|---|---|---|---|---|---|---|
| Val | Arg | Ala | Trp | Ile | Glu | Lys | Thr | Leu | Glu | Glu | Gly | Arg | Arg | Arg | Gly | |
| | | 435 | | | | | 440 | | | | | 445 | | | | |

| TAC | GTG | GAG | ACC | CTC | TTC | GGC | CGC | CGC | CGC | TAC | GTG | CCA | GAC | CTA | GAG | 1392 |
|---|---|---|---|---|---|---|---|---|---|---|---|---|---|---|---|---|
| Tyr | Val | Glu | Thr | Leu | Phe | Gly | Arg | Arg | Arg | Tyr | Val | Pro | Asp | Leu | Glu | |
| | 450 | | | | | 455 | | | | | 460 | | | | | |

| GCC | CGG | GTG | AAG | AGC | GTG | CGG | GAG | GCG | GCC | GAG | CGC | ATG | GCC | TTC | AAC | 1440 |

| Ala<br>465 | Arg | Val | Lys | Ser | Val<br>470 | Arg | Glu | Ala | Ala | Glu<br>475 | Arg | Met | Ala | Phe | Asn<br>480 | |
|---|---|---|---|---|---|---|---|---|---|---|---|---|---|---|---|---|
| ATG<br>Met | CCC<br>Pro | GTC<br>Val | CAG<br>Gln | GGC<br>Gly<br>485 | ACC<br>Thr | GCC<br>Ala | GCC<br>Ala | GAC<br>Asp | CTC<br>Leu<br>490 | ATG<br>Met | AAG<br>Lys | CTG<br>Leu | GCT<br>Ala | ATG<br>Met<br>495 | GTG<br>Val | 1488 |
| AAG<br>Lys | CTC<br>Leu | TTC<br>Phe | CCC<br>Pro<br>500 | AGG<br>Arg | CTG<br>Leu | GAG<br>Glu | GAA<br>Glu | ATG<br>Met<br>505 | GGG<br>Gly | GCC<br>Ala | AGG<br>Arg | ATG<br>Met | CTC<br>Leu<br>510 | CTT<br>Leu | CAG<br>Gln | 1536 |
| GTC<br>Val | CAC<br>His | GAC<br>Asp<br>515 | GAG<br>Glu | CTG<br>Leu | GTC<br>Val | CTC<br>Leu | GAG<br>Glu<br>520 | GCC<br>Ala | CCA<br>Pro | AAA<br>Lys | GAG<br>Glu | AGG<br>Arg<br>525 | GCG<br>Ala | GAG<br>Glu | GCC<br>Ala | 1584 |
| GTG<br>Val | GCC<br>Ala<br>530 | CGG<br>Arg | CTG<br>Leu | GCC<br>Ala | AAG<br>Lys | GAG<br>Glu<br>535 | GTC<br>Val | ATG<br>Met | GAG<br>Glu | GGG<br>Gly | GTG<br>Val<br>540 | TAT<br>Tyr | CCC<br>Pro | CTG<br>Leu | GCC<br>Ala | 1632 |
| GTG<br>Val<br>545 | CCC<br>Pro | CTG<br>Leu | GAG<br>Glu | GTG<br>Val | GAG<br>Glu<br>550 | GTG<br>Val | GGG<br>Gly | ATA<br>Ile | GGG<br>Gly | GAG<br>Glu<br>555 | GAC<br>Asp | TGG<br>Trp | CTC<br>Leu | TCC<br>Ser | GCC<br>Ala<br>560 | 1680 |
| AAG<br>Lys | GAG<br>Glu | TGA<br>* | | | | | | | | | | | | | | 1689 |

( 2 ) INFORMATION FOR SEQ ID NO: 3:

( i ) SEQUENCE CHARACTERISTICS:
        ( A ) LENGTH: 23 base pairs
        ( B ) TYPE: nucleic acid
        ( C ) STRANDEDNESS: single
        ( D ) TOPOLOGY: linear ( x i ) SEQUENCE DESCRIPTION: SEQ ID NO: 3:

GCTTGGGCAG AGGATCCGCC GGG         23

( 2 ) INFORMATION FOR SEQ ID NO: 4:

( i ) SEQUENCE CHARACTERISTICS:
        ( A ) LENGTH: 64 base pairs
        ( B ) TYPE: nucleic acid
        ( C ) STRANDEDNESS: single
        ( D ) TOPOLOGY: linear ( x i ) SEQUENCE DESCRIPTION: SEQ ID NO: 4:

GGGATGGCTA GCTCCTGGGA GAGGCGGTGG GCCGACATGC CGTAGAGGAC         50

CCCGTAGTTG ATGG         64

( 2 ) INFORMATION FOR SEQ ID NO: 5:

( i ) SEQUENCE CHARACTERISTICS:
        ( A ) LENGTH: 31 base pairs
        ( B ) TYPE: nucleic acid
        ( C ) STRANDEDNESS: single
        ( D ) TOPOLOGY: linear ( x i ) SEQUENCE DESCRIPTION: SEQ ID NO: 5:

GGAATTCCAT ATGGACGATC TGAAGCTCTC C         31

( 2 ) INFORMATION FOR SEQ ID NO: 6:

( i ) SEQUENCE CHARACTERISTICS:
        ( A ) LENGTH: 31 base pairs
        ( B ) TYPE: nucleic acid
        ( C ) STRANDEDNESS: single
        ( D ) TOPOLOGY: linear ( x i ) SEQUENCE DESCRIPTION: SEQ ID NO: 6:

GGGGTACCAA GCTTCACTCC TTGGCGGAGA G         31

( 2 ) INFORMATION FOR SEQ ID NO: 7:

( i ) SEQUENCE CHARACTERISTICS:
        ( A ) LENGTH: 31 base pairs
        ( B ) TYPE: nucleic acid
        ( C ) STRANDEDNESS: single
        ( D ) TOPOLOGY: linear ( x i ) SEQUENCE DESCRIPTION: SEQ ID NO: 7:

```
GGAATTCCAT ATGCTGGAGA GGCTTGAGTT T                               31
```

( 2 ) INFORMATION FOR SEQ ID NO: 8:

( i ) SEQUENCE CHARACTERISTICS:
        ( A ) LENGTH: 43 base pairs
        ( B ) TYPE: nucleic acid
        ( C ) STRANDEDNESS: single
        ( D ) TOPOLOGY: linear ( x i ) SEQUENCE DESCRIPTION: SEQ ID NO: 8:

```
GGAATTCCAT ATGCTGGAAC GTCTGGAGTT TGGCAGCCTC CTC                  43
```

( 2 ) INFORMATION FOR SEQ ID NO: 9:

( i ) SEQUENCE CHARACTERISTICS:
        ( A ) LENGTH: 46 base pairs
        ( B ) TYPE: nucleic acid
        ( C ) STRANDEDNESS: single
        ( D ) TOPOLOGY: linear ( x i ) SEQUENCE DESCRIPTION: SEQ ID NO: 9:

```
GGAATTCCAT ATGGCTCTGG AACGTCTGGA GTTTGGCAGC CTCCTC               46
```

( 2 ) INFORMATION FOR SEQ ID NO: 10:

( i ) SEQUENCE CHARACTERISTICS:
        ( A ) LENGTH: 40 base pairs
        ( B ) TYPE: nucleic acid
        ( C ) STRANDEDNESS: single
        ( D ) TOPOLOGY: linear ( x i ) SEQUENCE DESCRIPTION: SEQ ID NO: 10:

```
GGAATTCCAT ATGCTGGAAC GTCTGGAATT CGGCAGCCTC                      40
```

( 2 ) INFORMATION FOR SEQ ID NO: 11:

( i ) SEQUENCE CHARACTERISTICS:
        ( A ) LENGTH: 32 base pairs
        ( B ) TYPE: nucleic acid
        ( C ) STRANDEDNESS: single
        ( D ) TOPOLOGY: linear ( x i ) SEQUENCE DESCRIPTION: SEQ ID NO: 11:

```
GGGGTACCCT AACCCTTGGC GGAAAGCCAG TC                              32
```

( 2 ) INFORMATION FOR SEQ ID NO: 12:

( i ) SEQUENCE CHARACTERISTICS:
        ( A ) LENGTH: 64 base pairs
        ( B ) TYPE: nucleic acid
        ( C ) STRANDEDNESS: single
        ( D ) TOPOLOGY: linear ( x i ) SEQUENCE DESCRIPTION: SEQ ID NO: 12:

```
GGGATGGCTA GCTCCTGGGA GAGCCTATGG GCGGACATGC CGTAGAGGAC           50

GCCGTAGTTC ACCG                                                  64
```

( 2 ) INFORMATION FOR SEQ ID NO: 13:

( i ) SEQUENCE CHARACTERISTICS:
        ( A ) LENGTH: 35 base pairs
        ( B ) TYPE: nucleic acid
        ( C ) STRANDEDNESS: single
        ( D ) TOPOLOGY: linear ( x i ) SEQUENCE DESCRIPTION: SEQ ID NO: 13:

CTAGCTAGCC ATCCCCTACG AAGAAGCGGT GGCCT        35

( 2 ) INFORMATION FOR SEQ ID NO: 14:

( i ) SEQUENCE CHARACTERISTICS:
        ( A ) LENGTH: 1686 base pairs
        ( B ) TYPE: nucleic acid
        ( C ) STRANDEDNESS: single
        ( D ) TOPOLOGY: linear ( i x ) FEATURE:
        ( A ) NAME/KEY: FY4
        ( B ) LOCATION: 1...1683

( x i ) SEQUENCE DESCRIPTION: SEQ ID NO: 14:

```
ATG CTG GAA CGT CTG GAA TTC GGC AGC CTC CTC CAC GAG TTC GGC CTC        48
Met Leu Glu Arg Leu Glu Phe Gly Ser Leu Leu His Glu Phe Gly Leu
 1               5                  10                  15

CTG GAG GCC CCC GCC CCC CTG GAG GAG GCC CCC TGG CCC CCG CCG GAA        96
Leu Glu Ala Pro Ala Pro Leu Glu Glu Ala Pro Trp Pro Pro Pro Glu
                20                  25                  30

GGG GCC TTC GTG GGC TTC GTC CTC TCC CGC CCC GAG CCC ATG TGG GCG       144
Gly Ala Phe Val Gly Phe Val Leu Ser Arg Pro Glu Pro Met Trp Ala
            35                  40                  45

GAG CTT AAA GCC CTG GCC GCC TGC AGG GAC GGC CGG GTG CAC CGG GCA       192
Glu Leu Lys Ala Leu Ala Ala Cys Arg Asp Gly Arg Val His Arg Ala
        50                  55                  60

GCA GAC CCC TTG GCG GGC TAA AAG GAC CTC AAG GAG GTC CGG GGC CTC       240
Ala Asp Pro Leu Ala Gly Leu Lys Asp Leu Lys Glu Val Arg Gly Leu
65                  70                  75                  80

CTC GCC AAG GAC CTC GCC GTC TTG GCC TCG AGG GAG GGG CTA GAC CTC       288
Leu Ala Lys Asp Leu Ala Val Leu Ala Ser Arg Glu Gly Leu Asp Leu
                85                  90                  95

GTG CCC GGG GAC GAC CCC ATG CTC CTC GCC TAC CTC CTG GAC CCC TCC       336
Val Pro Gly Asp Asp Pro Met Leu Leu Ala Tyr Leu Leu Asp Pro Ser
               100                 105                 110

AAC ACC ACC CCC GAG GGG GTG GCG CGG CGC TAC GGG GGG GAG TGG ACG       384
Asn Thr Thr Pro Glu Gly Val Ala Arg Arg Tyr Gly Gly Glu Trp Thr
           115                 120                 125

GAG GAC GCC GCC CAC CGG GCC CTC CTC TCG GAG AGG CTC CAT CGG AAC       432
Glu Asp Ala Ala His Arg Ala Leu Leu Ser Glu Arg Leu His Arg Asn
       130                 135                 140

CTC CTT AAG CGC CTC GAG GGG GAG GAG AAG CTC CTT TGG CTC TAC CAC       480
Leu Leu Lys Arg Leu Glu Gly Glu Glu Lys Leu Leu Trp Leu Tyr His
145                 150                 155                 160

GAG GTG GAA AAG CCC CTC TCC CGG GTC CTG GCC CAC ATG GAG GCC ACC       528
Glu Val Glu Lys Pro Leu Ser Arg Val Leu Ala His Met Glu Ala Thr
               165                 170                 175

GGG GTA CGG CTG GAC GTG GCC TAC CTT CAG GCC CTT TCC CTG GAG CTT       576
Gly Val Arg Leu Asp Val Ala Tyr Leu Gln Ala Leu Ser Leu Glu Leu
           180                 185                 190

GCG GAG GAG ATC CGC CGC CTC GAG GAG GAG GTC TTC CGC TTG GCG GGC       624
Ala Glu Glu Ile Arg Arg Leu Glu Glu Glu Val Phe Arg Leu Ala Gly
       195                 200                 205
```

```
CAC  CCC  TTC  AAC  CTC  AAC  TCC  CGG  GAC  CAG  CTG  GAA  AGG  GTG  CTC  TTT      672
His  Pro  Phe  Asn  Leu  Asn  Ser  Arg  Asp  Gln  Leu  Glu  Arg  Val  Leu  Phe
     210                           215                      220

GAC  GAG  CTT  AGG  CTT  CCC  GCC  TTG  GGG  AAG  ACG  CAA  AAG  ACA  GGC  AAG      720
Asp  Glu  Leu  Arg  Leu  Pro  Ala  Leu  Gly  Lys  Thr  Gln  Lys  Thr  Gly  Lys
225                      230                      235                      240

CGC  TCC  ACC  AGC  GCC  GCG  GTG  CTG  GAG  GCC  CTA  CGG  GAG  GCC  CAC  CCC      768
Arg  Ser  Thr  Ser  Ala  Ala  Val  Leu  Glu  Ala  Leu  Arg  Glu  Ala  His  Pro
                         245                      250                      255

ATC  GTG  GAG  AAG  ATC  CTC  CAG  CAC  CGG  GAG  CTC  ACC  AAG  CTC  AAG  AAC      816
Ile  Val  Glu  Lys  Ile  Leu  Gln  His  Arg  Glu  Leu  Thr  Lys  Leu  Lys  Asn
               260                      265                      270

ACC  TAC  GTG  GAC  CCC  CTC  CCA  AGC  CTC  GTC  CAC  CCG  AGG  ACG  GGC  CGC      864
Thr  Tyr  Val  Asp  Pro  Leu  Pro  Ser  Leu  Val  His  Pro  Arg  Thr  Gly  Arg
          275                      280                      285

CTC  CAC  ACC  CGC  TTC  AAC  CAG  ACG  GCC  ACG  GCC  ACG  GGG  AGG  CTT  AGT      912
Leu  His  Thr  Arg  Phe  Asn  Gln  Thr  Ala  Thr  Ala  Thr  Gly  Arg  Leu  Ser
     290                      295                      300

AGC  TCC  GAC  CCC  AAC  CTG  CAG  AAC  ATC  CCC  GTC  CGC  ACC  CCC  TTG  GGC      960
Ser  Ser  Asp  Pro  Asn  Leu  Gln  Asn  Ile  Pro  Val  Arg  Thr  Pro  Leu  Gly
305                      310                      315                      320

CAG  AGG  ATC  CGC  CGG  GCC  TTC  GTG  GCC  GAG  GCG  GGT  TGG  GCG  TTG  GTG     1008
Gln  Arg  Ile  Arg  Arg  Ala  Phe  Val  Ala  Glu  Ala  Gly  Trp  Ala  Leu  Val
                         325                      330                      335

GCC  CTG  GAC  TAT  AGC  CAG  ATA  GAG  CTC  CGC  GTC  CTC  GCC  CAC  CTC  TCC     1056
Ala  Leu  Asp  Tyr  Ser  Gln  Ile  Glu  Leu  Arg  Val  Leu  Ala  His  Leu  Ser
               340                      345                      350

GGG  GAC  GAA  AAC  CTG  ATC  AGG  GTC  TTC  CAG  GAG  GGG  AAG  GAC  ATC  CAC     1104
Gly  Asp  Glu  Asn  Leu  Ile  Arg  Val  Phe  Gln  Glu  Gly  Lys  Asp  Ile  His
          355                      360                      365

ACC  CAG  ACC  GCA  AGC  TGG  ATG  TTC  GGC  GTC  CCC  CGA  GAG  GCC  GTG  GAC     1152
Thr  Gln  Thr  Ala  Ser  Trp  Met  Phe  Gly  Val  Pro  Pro  Glu  Ala  Val  Asp
370                      375                      380

CCC  CTG  ATG  CGC  CGG  GCG  GCC  AAG  ACG  GTG  AAC  TAC  GGC  GTC  CTC  TAC     1200
Pro  Leu  Met  Arg  Arg  Ala  Ala  Lys  Thr  Val  Asn  Tyr  Gly  Val  Leu  Tyr
385                      390                      395                      400

GGC  ATG  TCC  GCC  CAT  AGG  CTC  TCC  CAG  GAG  CTA  GCC  ATC  CCC  TAC  GAA     1248
Gly  Met  Ser  Ala  His  Arg  Leu  Ser  Gln  Glu  Leu  Ala  Ile  Pro  Tyr  Glu
                         405                      410                      415

GAA  GCG  GTG  GCC  TTT  ATA  GAG  CGC  TAC  TTC  CAA  AGC  TTC  CCC  AAG  GTG     1296
Glu  Ala  Val  Ala  Phe  Ile  Glu  Arg  Tyr  Phe  Gln  Ser  Phe  Pro  Lys  Val
               420                      425                      430

CGG  GCC  TGG  ATA  GAA  AAG  ACC  CTG  GAG  GAG  GGG  AGG  AAG  CGG  GGC  TAC     1344
Arg  Ala  Trp  Ile  Glu  Lys  Thr  Leu  Glu  Glu  Gly  Arg  Lys  Arg  Gly  Tyr
          435                      440                      445

GTG  GAA  ACC  CTC  TTC  GGA  AGA  AGG  CGC  TAC  GTG  CCC  GAC  CTC  AAC  GCC     1392
Val  Glu  Thr  Leu  Phe  Gly  Arg  Arg  Arg  Tyr  Val  Pro  Asp  Leu  Asn  Ala
450                      455                      460

CGG  GTG  AAG  AGC  GTC  AGG  GAG  GCC  GCG  GAG  CGC  ATG  GCC  TTC  AAC  ATG     1440
Arg  Val  Lys  Ser  Val  Arg  Glu  Ala  Ala  Glu  Arg  Met  Ala  Phe  Asn  Met
465                      470                      475                      480

CCC  GTC  CAG  GGC  ACC  GCC  GCC  GAC  CTC  ATG  AAG  CTC  GCC  ATG  GTG  AAG     1488
Pro  Val  Gln  Gly  Thr  Ala  Ala  Asp  Leu  Met  Lys  Leu  Ala  Met  Val  Lys
                         485                      490                      495

CTC  TTC  CCC  CGC  CTC  CGG  GAG  ATG  GGG  GCC  CGC  ATG  CTC  CTC  CAG  GTC     1536
Leu  Phe  Pro  Arg  Leu  Arg  Glu  Met  Gly  Ala  Arg  Met  Leu  Leu  Gln  Val
               500                      505                      510

CAC  GAC  GAG  CTC  CTC  CTG  GAG  GCC  CCC  CAA  GCG  CGG  GCC  GAG  GAG  GTG     1584
His  Asp  Glu  Leu  Leu  Leu  Glu  Ala  Pro  Gln  Ala  Arg  Ala  Glu  Glu  Val
          515                      520                      525
```

| | | | | | | | | | | | | | | | | |
|---|---|---|---|---|---|---|---|---|---|---|---|---|---|---|---|---|
| GCG | GCT | TTG | GCC | AAG | GAG | GCC | ATG | GAG | AAG | GCC | TAT | CCC | CTC | GCC | GTG | 1632 |
| Ala | Ala | Leu | Ala | Lys | Glu | Ala | Met | Glu | Lys | Ala | Tyr | Pro | Leu | Ala | Val | |
| | 530 | | | | | 535 | | | | | 540 | | | | | |
| CCC | CTG | GAG | GTG | GAG | GTG | GGG | ATG | GGG | GAG | GAC | TGG | CTT | TCC | GCC | AAG | 1680 |
| Pro | Leu | Glu | Val | Glu | Val | Gly | Met | Gly | Glu | Asp | Trp | Leu | Ser | Ala | Lys | |
| 545 | | | | | 550 | | | | | 555 | | | | | 560 | |
| GGT | TAG | | | | | | | | | | | | | | | 1686 |
| Gly | * | | | | | | | | | | | | | | | |

THERMOSTABLE DNA POLYMERASES

This application is a Continuation-in-Part application of U.S. Ser. No. 08/455,686, filed May 31, 1995, now abandoned.

BACKGROUND OF THE INVENTION

The present invention relates to novel thermo-stable DNA polymerases, the genes and vectors encoding them and their use in DNA sequencing.

U.S. Pat. Nos. 4,889,818 and 5,079,352 describe the isolation and expression of a DNA polymerase known as Taq DNA Polymerase (hereinafter referred to as Taq). It is reported that amino-terminal deletions wherein approximately one-third of the coding sequence is absent have resulted in producing a gene product that is quite active in polymerase assays. Taq is described as being of use in PCR (polymerase chain reaction).

U.S. Pat. No. 5,075,216 describes the use of Taq in DNA sequencing.

International patent application WO 92/06/06188 describes a DNA polymerase having an identical amino acid sequence to Taq except that it lacks the N-terminal 235 amino acids of Taq and its use in sequencing. This DNA polymerase is known as Δ Taq.

U.S. Pat. No. 4,795,699 describes the use of T7 type DNA polymerases (T7) in DNA sequencing. These are of great use in DNA sequencing in that they incorporate dideoxy nucleoside triphosphates (NTPs) with an efficiency comparable to the incorporation of deoxy NTPs; other polymerases incorporate dideoxy NTPs far less efficiently which requires comparatively large quantities of these to be present in sequencing reactions.

At the DOE Contractor-Grantee Workshop (Nov. 13–17, 1994, Santa Fe) and the I. Robert Lehman Symposium (Nov. 11–14, 1994, Sonoma), Prof. S. Tabor identified a site in DNA polymerases that can be modified to incorporate dideoxy NTPs more efficiently. He reported that the presence or absence of a single hydroxy group (tyrosine vs. phenylalanine) at a highly conserved position on E. coli, DNA Polymerase I, T7, and Taq makes more than a 1000-fold difference in their ability to discriminate against dideoxy NTPs. (See also European Patent Application 94203433.1 published May 31, 1995, Publication No. 0 655 506 A1 and hereby incorporated by reference herein.)

SUMMARY OF THE INVENTION

The present invention provides a DNA polymerase having an amino acid sequence differentiated from Taq in that it lacks the N-terminal 272 amino acids and has the phenylalanine at position 667 (of native Taq) replaced by tyrosine. Preferably, the DNA polymerase has methionine at position 1 (equivalent to position 272 of Taq) (hereinafter referred to as FY2) The full DNA sequence is given as FIG. 1 (SEQ. ID. NO. 1). Included within the scope of the present invention are DNA polymerases having substantially identical amino acid sequences to the above which retain thermostability and efficient incorporation of dideoxy NTPs.

By a substantially identical amino acid sequence is meant a sequence which contains 540 to 582 amino acids that may have conservative amino acid changes compared with Taq which do not significantly influence thermostability or nucleotide incorporation, i.e. other than the phenylalanine to tyrosine conversion. Such changes include substitution of like charged amino acids for one another, or amino acids with small side chains for other small side chains, e.g., ala for val. More drastic changes may be introduced at noncritical regions where little or no effect on polymerase activity is observed by such a change.

The invention also features DNA polymerases that lack between 251 and 293 (preferably 271 or 272) of the N-terminal amino acids of Thermus flavus (Tfl) and have the phenylalanine at position 666 (of native Tfl) replaced by tyrosine; and those that lack between 253 and 295 (preferably 274) of the N-terminal amino acids of Thermus thermophilus (Tth) and have the phenylalanine at position 669 (of native Tth) replaced by tyrosine.

By efficient incorporation of dideoxy NTPs is meant the ability of a polymerase to show little, if any, discrimination in the incorporation of ddNTPs when compared with dNTPs. Suitably efficient discrimination is less than 1:10 and preferably less than 1:5. Such discrimination can be measured by procedures known in the art.

One preferred substantially identical amino acid sequence to that given above is that which contains 562 amino acids having methionine at position 1 and alanine at position 2 (corresponding to positions 271 and 272 of native Taq) (hereinafter referred to as FY3). A full DNA sequence is given as FIG. 2. This is a preferred DNA polymerase for expression by a gene of the present invention.

The purified DNA polymerases FY2 and FY3 both give a single polypeptide band on SDS polyacrylamide gels, unlike Δ Taq, having either a phenylalanine or tyrosine at position 667 which forms several polypeptide bands of similar size on SDS polyacrylamide gels.

A second preferred substantially identical amino acid sequence is that which lacks 274 of the N-terminal amino acids of Thermus thermophilus having methionine at position 1, and the phenylalanine to tyrosine mutation at position 396 (corresponding to position 669 of native Tth) (hereinafter referred to as FY4). A full DNA sequence is given as FIG. 5 (SEQ. ID. NO. 14).

The present invention also provides a gene encoding a DNA polymerase of the present invention. In order to assist in the expression of the DNA polymerase activity, the modified gene preferably codes for a methionine residue at position 1 of the new DNA polymerase. In addition, in one preferred embodiment of the invention, the modified gene also codes for an alanine at position 2 (corresponding to position 272 of native Taq).

In a further aspect, the present invention provides a vector containing the gene encoding the DNA polymerase activity of the present invention, e.g., encoding an amino acid sequence differentiated from native Taq in that it lacks the N-terminal 272 amino acids and has phenylalanine at position 396 (equivalent to position 667 of Taq) replaced by tyrosine or a substantially identical amino acid sequence thereto.

In a yet further aspect, the present invention provides a host cell comprising a vector containing the gene encoding the DNA polymerase activity of the present invention, e.g., encoding an amino acid sequence differentiated from native Taq in that it lacks the N-terminal 272 amino acids and has phenylalanine at position 396 (equivalent to position 667 of native Taq) replaced by tyrosine or a substantially identical amino acid sequence thereto.

The DNA polymerases of the present invention are preferably in a purified form. By purified form is meant that the DNA polymerase is isolated from a majority of host cell proteins normally associated with it; preferably the polymerase is at least 10% (w/w) of the protein of a preparation, even more preferably it is provided as a homogeneous preparation, e.g., a homogeneous solution. Preferably the DNA polymerase is a single polypeptide on an SDS polyacrylamide gel.

The DNA polymerases of the present invention are suitably used in sequencing, preferably in combination with a pyrophosphatase. Accordingly, the present invention provides a composition which comprises a DNA polymerase of the present invention in combination with a pyrophosphatase, preferably a thermostable pyrophosphatase such as *Thermoplasma acidophilum* pyrophosphatase. (Schafer, G. and Richter, O. H. (1992) *Eur. J. Biochem.* 209, 351–355).

The DNA polymerases of the present invention can be constructed using standard techniques. By way of example, mutagenic PCR primers can be designed to incorporate the desired Phe to Tyr amino acid change (FY mutation) in one primer. In our hands these primers also carried restriction sites that are found internally in the sequence of the Taq polymerase gene clone of Delta Taq, pWB253, which was used by us as template DNA. However, the same PCR product can be generated with this primer pair from any clone of Taq or with genomic DNA isolated directly from *Thermus aquaticus*. The PCR product encoding only part of the gene is then digested with the appropriate restriction enzymes and used as a replacement sequence for the clone of Delta Taq digested with the same restriction enzymes. In our hands the resulting plasmid was designated pWB253Y. The presence of the mutation can be verified by DNA sequencing of the amplified region of the gene.

Further primers can be prepared that encode for a methionine residue at the N-terminus that is not found at the corresponding position of Taq, the sequence continuing with amino acid residue 273. These primers can be used with a suitable plasmid, e.g., pWB253Y DNA, as a template for amplification and the amplified gene inserted into a vector, e.g., pRE2, to create a gene, e.g., pRE273Y, encoding the polymerase (FY2). The entire gene can be verified by DNA sequencing.

Improved expression of the DNA polymerases of the present invention in the pRE2 expression vector was obtained by creating further genes, pREFY2pref (encoding a protein identical to FY2) and pREFY3 encoding FY3. A mutagenic PCR primer was used to introduce silent codon changes (i.e., the amino acid encoded is not changed) at the amino terminus of the protein which did not affect the sequence of the polypeptide. These changes led to increased production of FY2 polymerase. FY3 was designed to promote increased translation efficiency in vivo. In addition to the silent codon changes introduced in pREFY2pref, a GCT codon was added in the second position (SEQ. ID. NO. 2), as occurs frequently in strongly expressed genes in *E. coli*. This adds an amino acid to the sequence of FY2, and hence the protein was given its own designation FY3. Both constructs produce more enzyme than pRE273Y.

Silent codon changes such as the following increase protein production in *E. coli:* substitution of the codon GAG for GAA;
substitution of the codon AGG, AGA, CGG or CGA for CGT or CGC;
substitution of the codon CTT, CTC, CTA, TTG or TTA for CTG;
substitution of the codon ATA for ATT or ATC;
substitution of the codon GGG or GGA for GGT or GGC.

The present invention also provides a method for determining the nucleotide base sequence of a DNA molecule.

The method includes providing a DNA molecule annealed with a primer molecule able to hybridize to the DNA molecule; and incubating the annealed molecules in a vessel containing at least one deoxynucleotide triphosphate, and a DNA polymerase of the present invention. Also provided is at least one DNA synthesis terminating agent which terminates DNA synthesis at a specific nucleotide base. The method further includes separating the DNA products of the incubating reaction according to size, whereby at least a part of the nucleotide base sequence of the DNA molecule can be determined.

In preferred embodiments, the sequencing is performed at a temperature above 50° C., 60° C., or 70° C.

In other preferred embodiments, the DNA polymerase has less than 1000, 250, 100, 50, 10 or even 2 units of exonuclease activity per mg of polymerase (measured by standard procedure, see below) and is able to utilize primers having only 4, 6 or 10 bases; and the concentration of all four deoxynucleoside triphosphates at the start of the incubating step is sufficient to allow DNA synthesis to continue until terminated by the agent, e.g., a ddNTP.

For cycle sequencing, the DNA polymerases of the present invention make it possible to use significantly lower amounts of dideoxynucleotides compared to naturally occurring enzymes. That is, the method involves providing an excess amount of deoxynucleotides to all four dideoxynucleotides in a cycle sequencing reaction, and performing the cycle sequencing reaction.

Preferably, more than 2, 5, 10 or even 100 fold excess of a dNTP is provided to the corresponding ddNTP.

In a related aspect, the invention features a kit or solution for DNA sequencing including a DNA polymerase of the present invention and a reagent necessary for the sequencing such as dITP, deaza GTP, a chain terminating agent such as a ddNTP, and a manganese-containing solution or powder and optionally a pyrophosphatase.

In another aspect, the invention features a method for providing a DNA polymerase of the present invention by providing a nucleic acid sequence encoding the modified DNA polymerase, expressing the nucleic acid within a host cell, and purifying the DNA polymerase from the host cell.

In another related aspect, the invention features a method for sequencing a strand of DNA essentially as described above with one or more (preferably 2, 3 or 4) deoxyribonucleoside triphosphates, a DNA polymerase of the present invention, and a first chain terminating agent. The DNA polymerase causes the primer to be elongated to form a first series of first DNA products differing in the length of the elongated primer, each first DNA product having a chain terminating agent at its elongated end, and the number of molecules of each first DNA products being approximately the same for substantially all DNA products differing in length by no more than 20 bases. The method also features providing a second chain terminating agent in the hybridized mixture at a concentration different from the first chain terminating agent, wherein the DNA polymerase causes production of a second series of second DNA products differing in the length of the elongated primer, with each second DNA product having the second chain terminating agent at its elongated end. The number of molecules of each second DNA product is approximately the same for substantially all second DNA products differing in length from each other by from 1 to 20 bases, and is distinctly different from the number of molecules of all the first DNA products having a length differing by no more than 20 bases from that of said second DNA products.

In preferred embodiments, three or four such chain terminating agents can be used to make different products and the sequence reaction is provided with a magnesium ion, or even a manganese or iron ion (e.g., at a concentration between 0.05 and 100 mM, preferably between 1 and 10 mM); and the DNA products are separated according to molecular weight in four or less lanes of a gel.

In another related aspect, the invention features a method for sequencing a nucleic acid by combining an oligonucleotide primer, a nucleic acid to be sequenced, between one and four deoxyribonucleoside triphosphates, a DNA polymerase of the present invention, and at least two chain terminating agents in different amounts, under conditions favoring extension of the oligonucleotide primer to form nucleic acid fragments complementary to the nucleic acid to be sequenced. For example, the chain terminating agent may be a dideoxynucleotide terminator for adenine, guanine, cytosine or thymine. The method further includes separating the nucleic acid fragments by size and determining the nucleic acid sequence. The agents are differentiated from each other by intensity of a label in the primer extension products.

While it is common to use gel electrophoresis to separate DNA products of a DNA sequencing reaction, those in the art will recognize that other methods may also be used. Thus, it is possible to detect each of the different fragments using procedures such as time of flight mass spectrometry, electron microscopy, and single molecule detection methods.

The invention also features an automated DNA sequencing apparatus having a reactor including reagents which provide at least two series of DNA products formed from a single primer and a DNA strand. Each DNA product of a series differs in molecular weight and has a chain terminating agent at one end. The reagents include a DNA polymerase of the present invention. The apparatus includes a separating means for separating the DNA product along one axis of the separator to form a series of bands. It also includes a band reading means for determining the position and intensity of each band after separation along the axis, and a computing means that determines the DNA sequence of the DNA strand solely from the position and intensity of the bands along the axis and not from the wavelength of emission of light from any label that may be present in the separating means.

Other features and advantages of the invention will be apparent from the following description of the preferred embodiments thereof, and from the claims.

DESCRIPTION OF THE PREFERRED EMBODIMENTS

The drawings will first briefly be described.

DRAWINGS

Figure 1A:
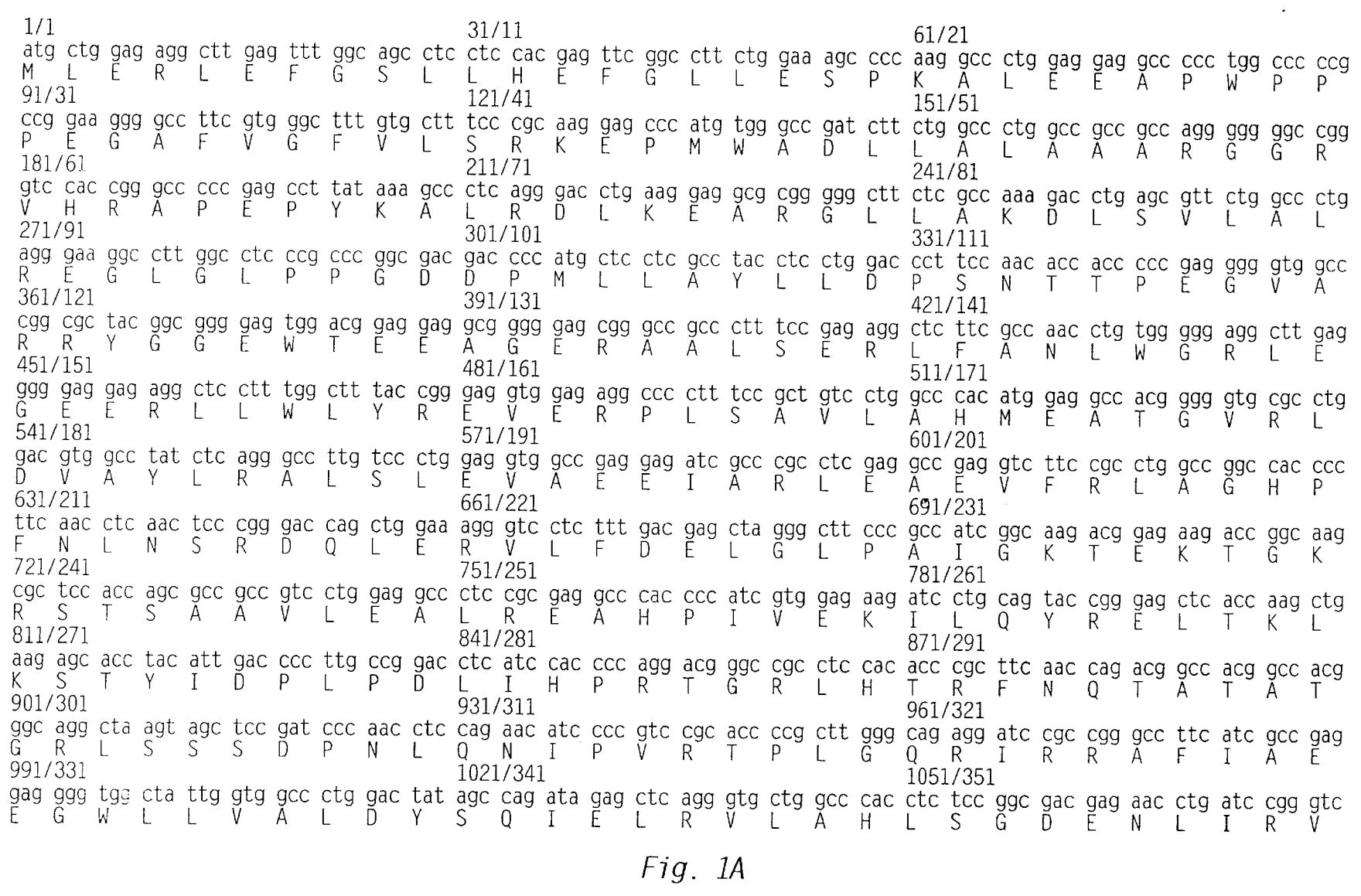
Figure 2A:
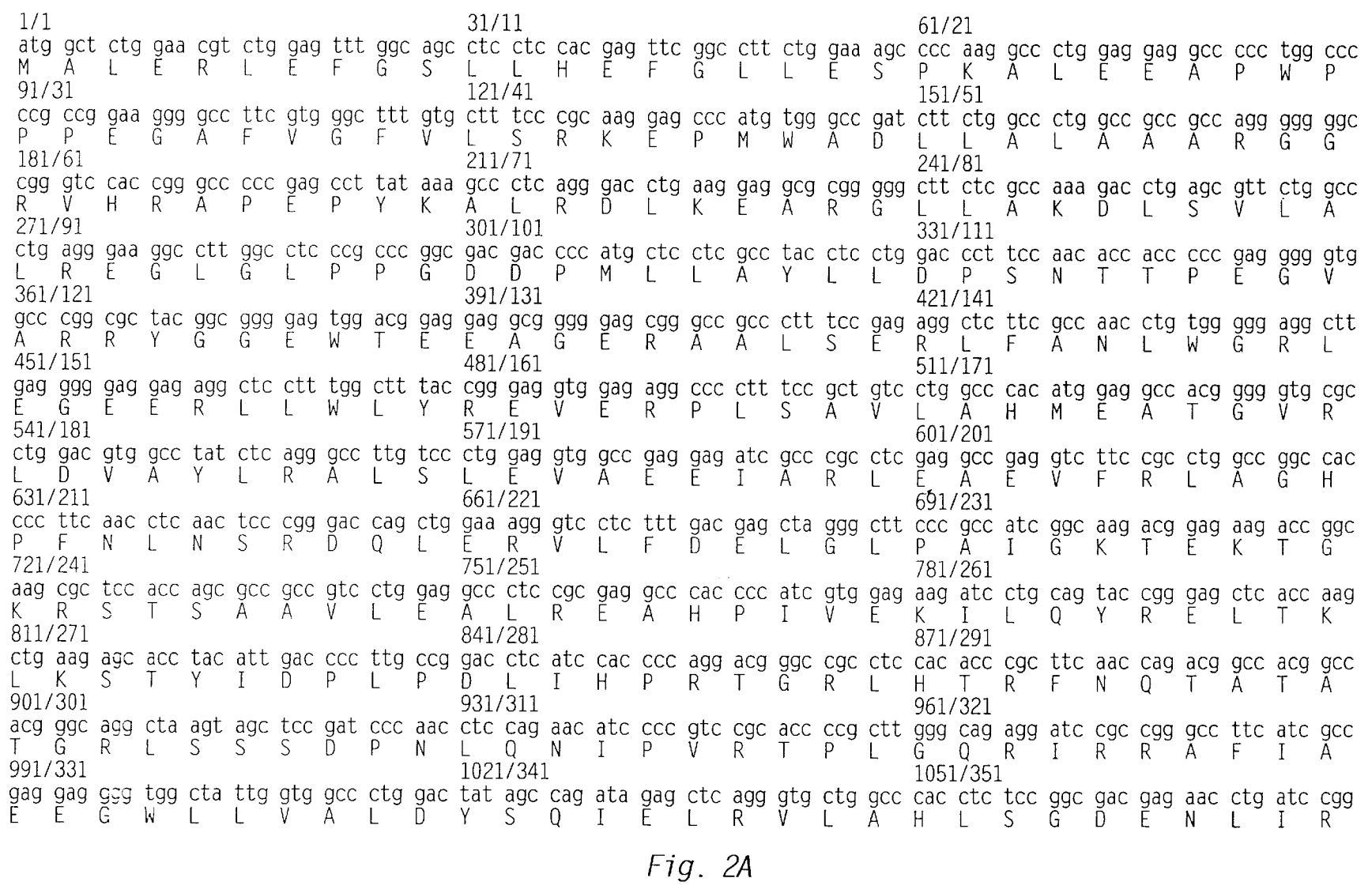
Figure 3A:
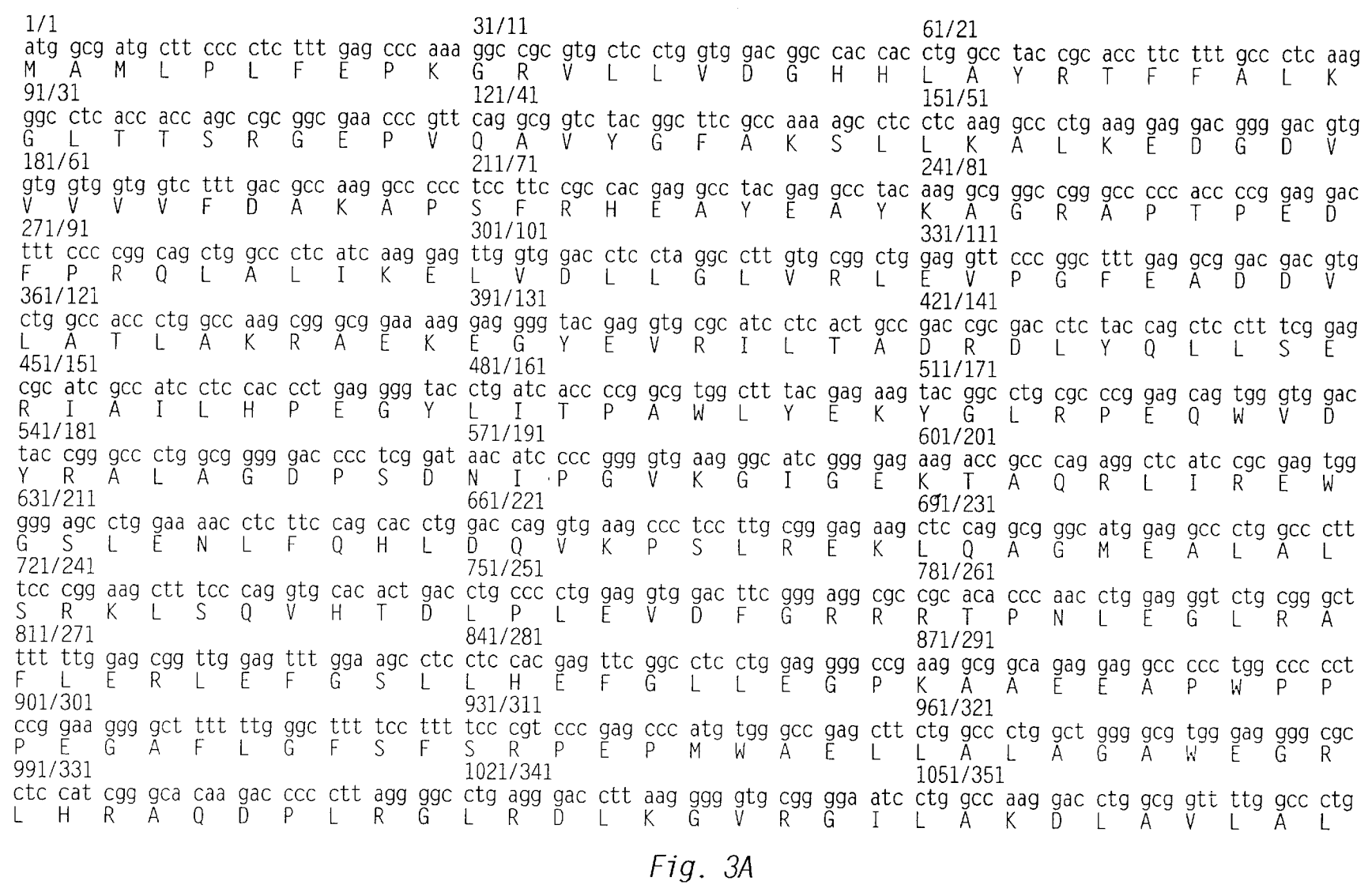
Figure 3B:
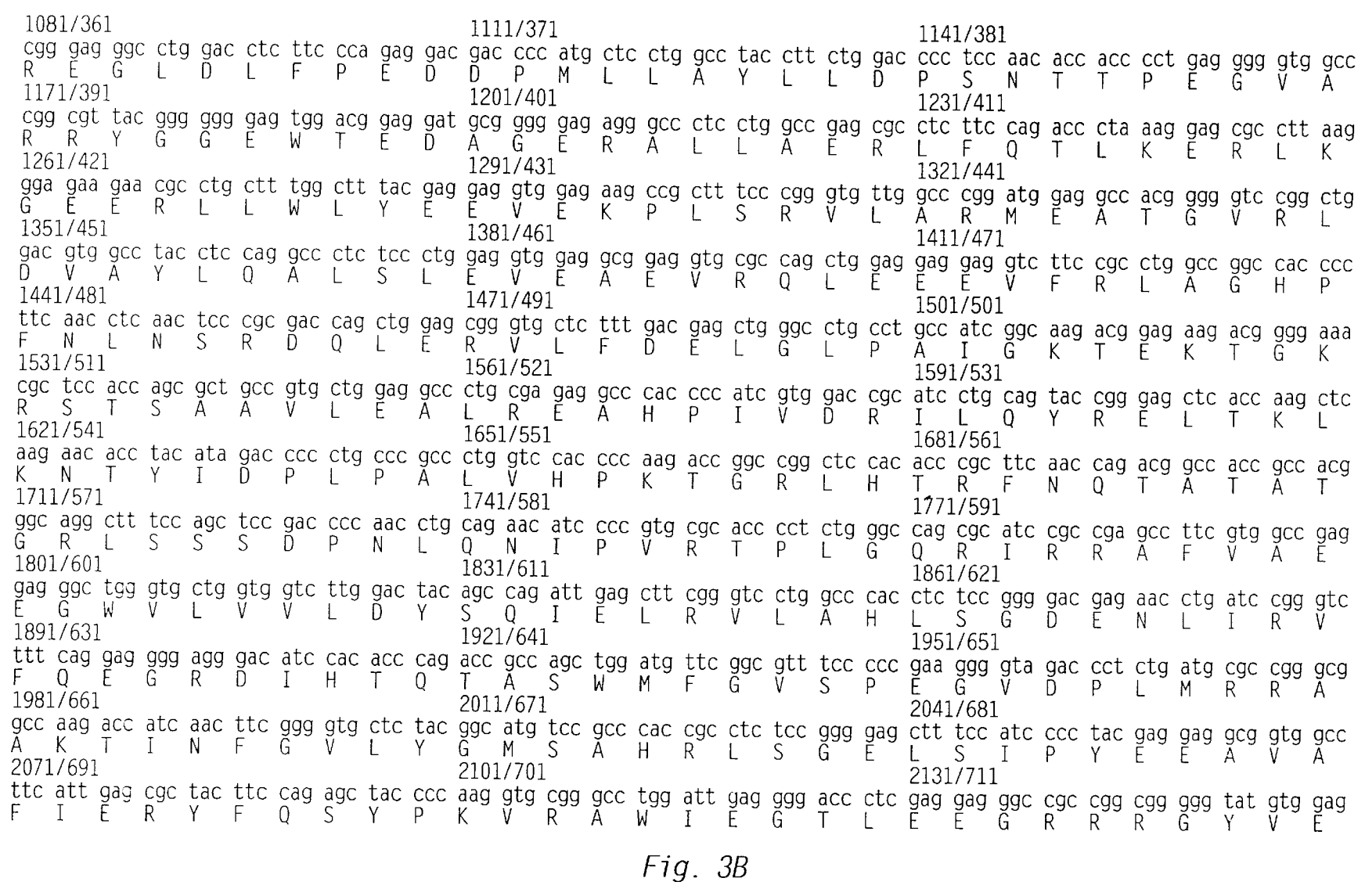
Figure 4A:
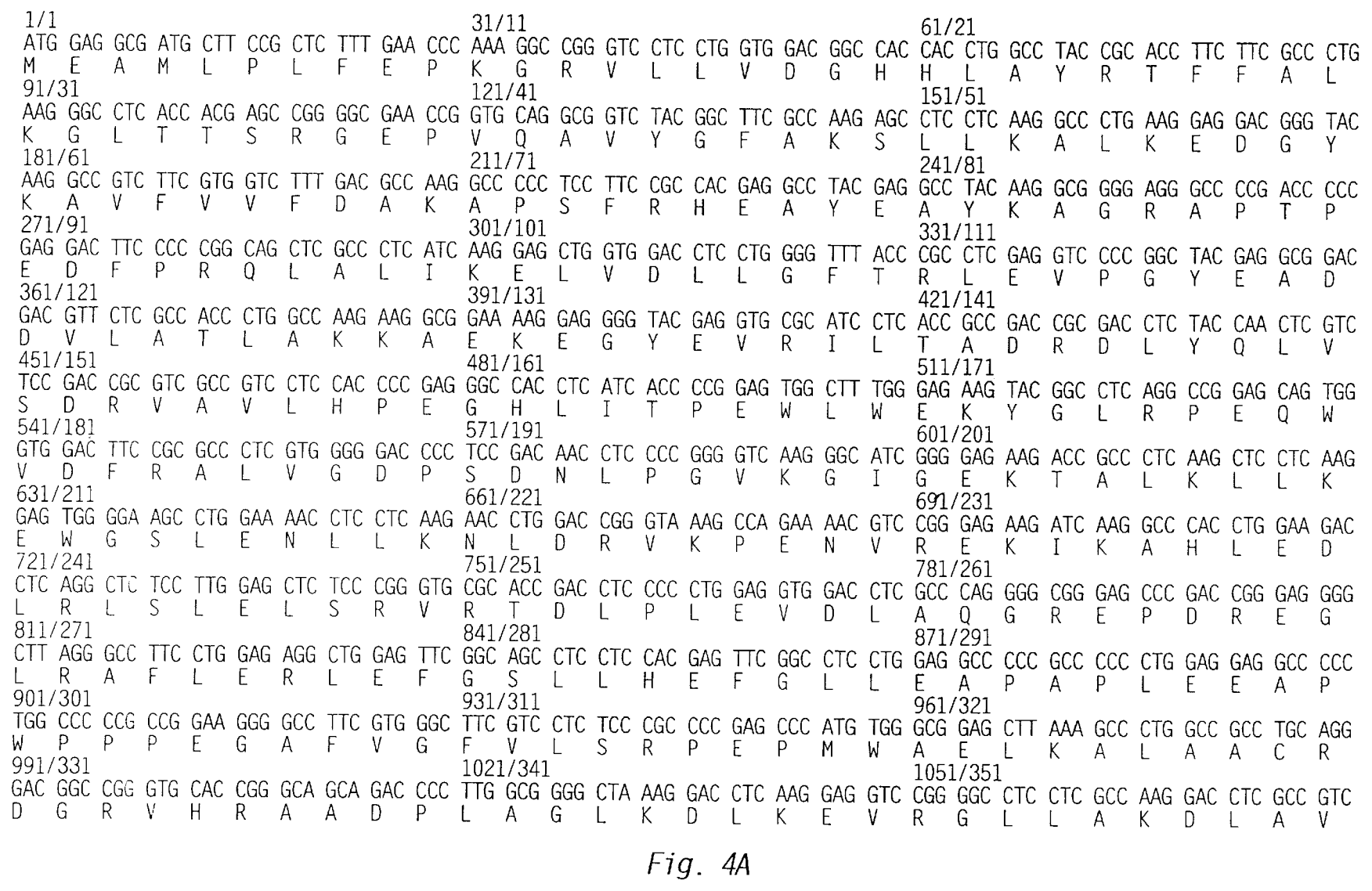
Figure 4B:
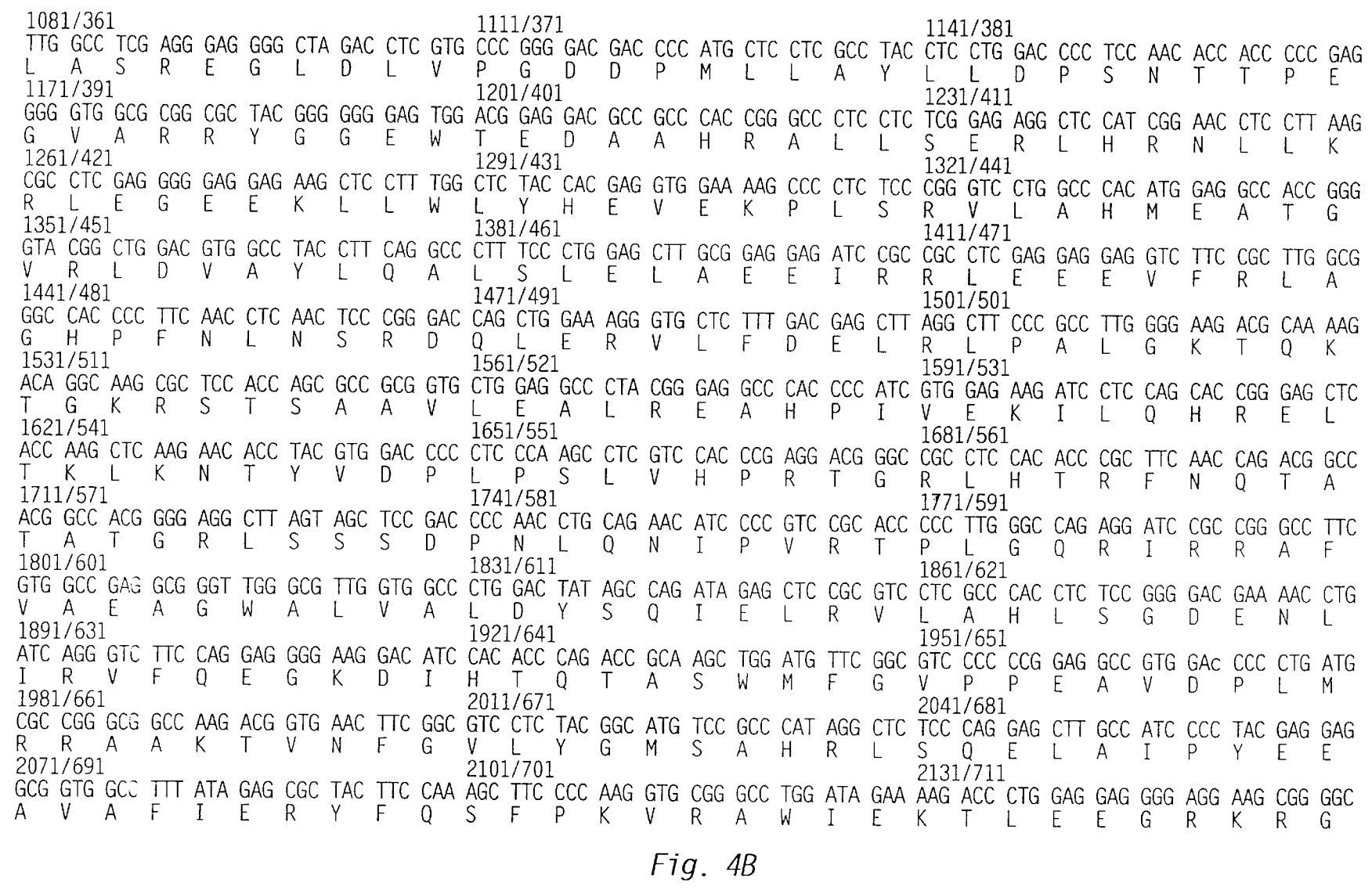
Figure 5A:
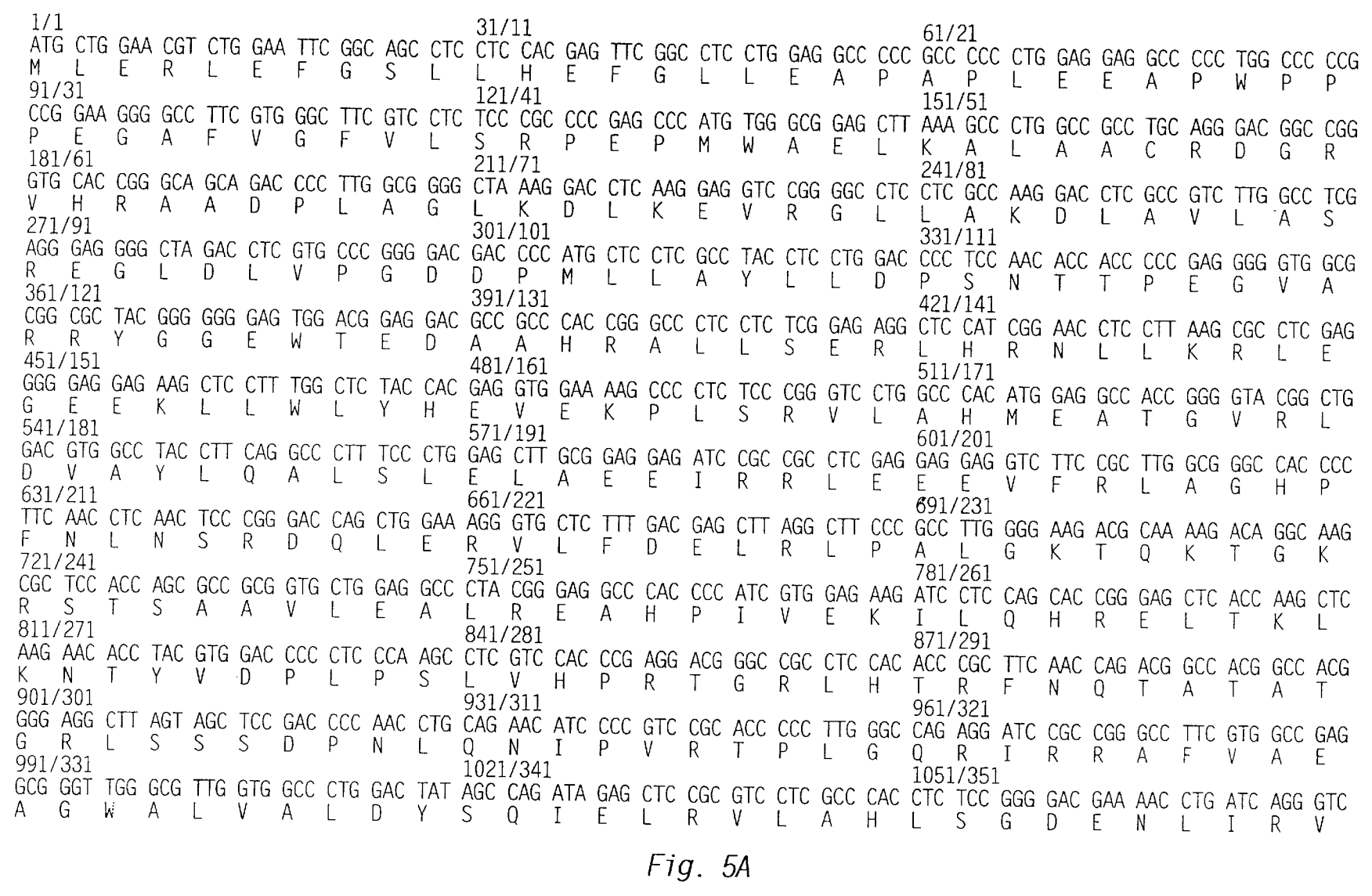

FIGS. 1–4 are the DNA sequences, and corresponding amino acid sequences, of FY2, FY3, and the DNA polymerases of *T. flavus* and *Thermus thermophilus*, respectively. FIG. 5 is the DNA sequence and corresponding amino acid sequence of FY4.

EXAMPLES

The following examples serve to illustrate the DNA polymerases of the present invention and their use in sequencing.

Preparation of FY DNA Polymerases (FY2 and FY3)

Bacterial Strains

*E. coli* strains: MV1190 [Δ(srl-recA) 306::Tn10, Δ(lac-proAB), thi, supE, F' (traD36 proAB+ lacI$^q$ lacZ ΔM15)]; DHλ+ [gyrA96, recA1, relA1, endA1, thi-1, hsdR17, supE44, λ+1; $^M$5248 [λ(bio275, cI857, cIII+, N+, Δ(H1))].

PCR

Reaction conditions based on the procedure of Barnes (91 *Proc. Nat'l. Acad. Sci.* 2216–2220, 1994) were as follows: 20 mM Tricine pH8.8, 85 mM KOAc, 200 mM dNTPs, 10% glycerol, 5% DMSO, 0.5 mM each primer, 1.5 mM MgOAc, 2.5 U HotTub (Amersham Life Science Inc.), 0.025 U DeepVent (New England Biolabs), 1–100 ng target DNA per 100 ml reaction. Cycling conditions were 94° C. 30 s, 68° C. 10 m40 s for 8 cycles; then 94° C. 30 s, 68° C. 12 m00 s for 8 cycles; then 94° C. 30 s, 68° C. 13 m20 s for 8 cycles; then 94° C. 30 s, 68° C. 14 m40 s for 8 cycles.

In vitro mutagenesis

Restriction enzyme digestions, plasmid preparations, and other in vitro manipulations of DNA were performed using standard protocols (Sambrook et al., Molecular Cloning 2nd Ed. Cold Spring Harbor Press, 1989). PCR (see protocol above) was used to introduce a Phe to Tyr amino acid change at codon 667 of native Taq DNA polymerase (which is codon 396 of FY2). Oligonucleotide primer 1 dGCT-TGGGCAGAGGATCCGCCGGG (SEQ. ID. NO. 3) spans nucleotides 954 to 976 of the coding region of SEQ. ID. NO. 1 including a BamHI restriction site. Mutagenic oligo primer 2 dGGGATGGCTAGCTCCTGGGAGAGGCG-GTGGGCCGACATGCCGTAGA GGACCCCGTAGT-TGATGG (SEQ. ID. NO. 4) spans nucleotides 1178 to 1241 including an NheI site and codon 396 of Sequence ID. NO. 1. A clone of exo⁻ Taq deleted for the first 235 amino acids, pWB253 encoding DeltaTaq polymerase (Barnes, 112 *Gene* 29–35, 1992) was used as template DNA. Any clone of Taq polymerase or genomic DNA from *Thermus aguaticus* could also be utilized to amplify the identical PCR product. The PCR product was digested with BamHI and NheI, and this fragment was ligated to BamHI/NheI digested pWB253 plasmid to replace the corresponding fragment to create pWB253Y, encoding polymerase FY1. Cells of *E. coli* strain MV1190 were used for transformation and induction of protein expression, although any host strain carrying a lac repressor could be substituted. DNA sequencing verified the Phe to Tyr change in the coding region.

PCR primer 3 dGGAATTCCATATGGACGATCT-GAAGCTCTCC (SEQ. ID. NO. 5) spanning the start codon and containing restriction enzyme sites, was used with PCR primer 4 dGGGGTACCAAGCTTCACTCCTTGGCG-GAGAG (SEQ. ID. NO. 6) containing restriction sites and spanning the stop codon (codon 562 of Sequence ID. NO. 1). A methionine start codon and restriction enzyme recognition sequences were added to PCR primer 5 dGGAATTC-CATATGCTGGAGAGGCTTGAGTTT (SEQ. ID. NO. 7), which was used with primer 4 above. PCR was performed using the above primer pairs, and plasmid pWB253Y as template. The PCR products were digested with restriction enzymes NdeI and KpnI and ligated to NdeI/KpnI digested vector pRE2 (Reddi et al., 17 *Nucleic Acids Research* 10,473–10,488, 1989) to make plasmids pRE236Y, encoding FY1 polymerase, and pRE273Y encoding FY2 polymerase, respectively. Cells of *E. coli* strain DHλ+ were used for primary transformation with this and all subsequent pRE2 constructions, and strain M5248 (λcI857) was used for protein expression, although any comparable pair of *E. coli* strains carrying the cI+ and cI857 alleles could be utilized. Alternatively, any rec+ cI+ strain could be induced by chemical agents such as nalidixic acid to produce the polymerase. The sequences of both genes were verified. pRE273Y was found to produce a single polypeptide band on SDS polyacrylamide gels, unlike pRE253Y or pRE236Y.

Primer 6 dGGAATTCCATATGCTGGAACGTCTG-GAGTTTGGCAGCCTC CTC (SEQ. ID. NO. 8) and primer 4 were used to make a PCR product introducing silent changes in codon usage of FY2. The product was digested with NdeI/BamHI and ligated to a pRE2 construct containing the 3' end of FY2 to create pREFY2pref, encoding FY2 DNA polymerase. Primer 7 dGGAATTCCATATG-GCTCTGGAACGTCTGGAGTTTGGCAGCCTCCTC (SEQ. ID. NO. 9) and primer 4 were used to make a PCR product introducing an additional alanine codon commonly occurring at the second position of highly expressed genes. The NdeI/BamHI digested fragment was used as above to create pREFY3, encoding FY3 DNA polymerase.

Preparation of FY4 DNA Polymerase

Bacterial Strains

E. coli strains: DH1λ$^+$ [gyrA96, recA1, relA1, endA1, thi-1, hsdR17, supE44, λ$^+$]; M5248 [λ (bio275, cI857, cIII+, N+, Δ (H1))].

PCR

Genomic DNA was prepared by standard techniques from *Thermus thermophilus*. The DNA polymerase gene of *Thermus thermophilus* is known to reside on a 3 kilobase AlwNI fragment. To enrich for polymerase sequences in some PCR reactions, the genomic DNA was digested prior to PCR with AlwNI, and fragments of approximately 3 kb were selected by agarose gel electrophoresis to be used as template DNA. Reaction conditions were as follows: 10 mM Tris pH8.3, 50 mM KCl, 800 μM dNTPs, 0.001% gelatin, 1.0 μM each primer, 1.5 mM MgCl$_2$, 2.5 U Tth, 0.025 U DeepVent (New England Biolabs), per 100 μl reaction. Cycling conditions were 94° C. 2 min, then 35 cycles of 94° C. 30 s, 55° C. 30 s, 72° C. 3 min, followed by 72° C. for 7 min.

In vitro mutagenesis

Restriction enzyme digestions, plasmid preparations, and other in vitro manipulations of DNA were performed using standard protocols (Sambrook et al., 1989). Plasmid pMR1 was constructed to encode an exonuclease-free polymerase, with optimized codons for expression in *E. coli* at the 5' end. Primer 8 (SEQ. ID. NO. 10) (GGAATTCCATATGCT GGAACGTCTGGAATTCGGCAGCCTC) was used with Primer 9 (SEQ. ID. NO.11) (GGGGTACCCTAA CCCTTGGCGGAAAGCCAGTC) to create a PCR product from Tth genomic DNA, which was digested with restriction enzymes NdeI and KpnI and inserted into plasmid pRE2 (Reddi et al., 1989, *Nucleic Acids Research* 17, 10473–10488) digested with the same enzymes.

To create the desired F396Y mutation, two PCR products were made from Tth chromosomal DNA. Primer 8 above was used in combination with Primer 10 (SEQ. ID. NO. 12) (GGGATGGCTAGCTCCTGGGAGAGCCTATGGGCG GACAT GCCGTAGAGGACGCCGTAGTTCACCG) to create a portion of the gene containing the F to Y amino acid change as well as a silent change to create an NheI restriction site. Primer 11 (SEQ. ID. NO. 13) (CTAGCTAGCCATCCCCTACGAAGAAGCGGT GGCCT) was used in combination with primer 9 above to create a portion of the gene from the introduced NheI site to the stop codon at the 3' end of the coding sequence. The PCR product of Primers 8 and 10 was digested with NdeI and NheI, and the PCR product of Primers 9 and 11 was digested with NheI and KpnI. These were introduced into expression vector pRE2 which was digested with NdeI and KpnI to produce plasmid pMR5. In addition to the desired changes, pMR5 was found to have a spurious change introduced by PCR, which led to an amino acid substitution, K234R. Plasmid pMR8 was created to eliminate this substitution, by replacing the AflII/BamHI fragment of pMR5 for the corresponding fragment from pMR1. The FY4 polymerase encoded by plasmid pMR8 (SEQ. ID. NO. 14) is given in FIG. 5.

Cells of *E. coli* strain DH1λ$^+$ were used for primary transformation, and strain M5248 (λcI857) was used for protein expression, although any comparable pair of *E. coli* strains carrying the cI$^+$ and cI857 alleles could be utilized. Alternatively, any rec$^+$ cI$^+$ strain could be induced by chemical agents such as nalidixic acid to produce the polymerase.

Protein Sequencing

Determinations of amino terminal protein sequences were performed at the W. M. Keck Foundation, Biotechnology Resource Laboratory, New Haven, Conn.

Purification of Polymerases

A 1 liter culture of 2×LB (2% Bacto-Tryptone, 1% Bacto-Yeast Extract, 0.5% NaCl)+0.2% Casamino Acids+20 mM KPO$_4$ pH 7.5+50 μg/ml Ampicillin was inoculated with a glycerol stock of the appropriate cell strain and grown at 30° C. with agitation until cells were in log phase (0.7–1.0 OD$_{590}$). 9 liters of 2×LB+0.2% Casamino Acids +20 mM KPO$_4$ pH 7.5+0.05% Mazu Anti-foam was inoculated with 1 liter of log phase cells in 10 liter Microferm Fermentors (New Brunswick Scientific Co.). Cells were grown at 30° C. under 15 psi pressure, 350–450 rpm agitation, and an air flow rate of 14,000 cc/min±1000 cc/min. When the OD$_{590}$ reached 1.5–2.0, the cultures were induced by increasing the temperature to 40°–42° C. for 90–120 minutes. The cultures were then cooled to <20° C. and the cells harvested by centrifugation in a Sorvall RC-3B centrifuge at 5000 rpm at 4° C. for 15–20 minutes. Harvested cells were stored at −80° C.

Frozen cells were broken into small pieces and resuspended in pre-warmed (90°–95° C.) Lysis Buffer (20 mM Tris pH 8.5, 1 mM EDTA, 10 mM MgCl$_2$, 16 mM (NH$_4$)$_2$SO$_4$, 0.1% Tween 20, 0.1% Nonidet P-40, 1 mM PMSF). Resuspended cells were then heated rapidly to 80° C. and incubated at 80° C. for 20 minutes with constant stirring. The suspension was then rapidly cooled on ice. The cell debris was removed by centrifugation using a Sorvall GSA rotor at 10,000 rpm for 20 minutes at 4° C. The NaCl concentration of the supernatant was adjusted to 300 mM. The sample was then passed through a diethylaminoethyl cellulose (Whatman DE-52) column that had been previously equilibrated with Buffer A (20 mM Tris pH 8.5, 1 mM EDTA, 0.1% Tween 20, 0.1% Nonidet P-40, 300 mM NaCl, 10% glycerol, 1 mM DTT), and polymerase collected in the flow through. The sample was then diluted to a concentration of NaCl of 100 mM and applied to a Heparin-sepharose column. The polymerase was eluted from the column with a NaCl gradient (100–500 mM NaCl). The sample was then dialyzed against Buffer B (20 mM Tris pH 8.5, 1 mM EDTA, 0.1% Tween 20, 0.1% Nonidet P-40, 10 mM KCl, 10% glycerol, 1 mM DTT) and further diluted as needed to lower the conductivity of the sample to the conductivity of Buffer B. The sample was then applied to a diethylaminoethyl (Waters DEAE 15 HR) column and eluted with a 10–500 mM KCl gradient. The polymerase was then diluted with an equal volume of Final Buffer (20 mM Tris pH 8.5, 0.1 mM EDTA, 0.5% Tween 20, 0.5% Nonidet P-40, 100 mM KCl, 50% glycerol, 1 mM DTT) and dialyzed against Final Buffer.

Assay of Exonuclease Activity

The exonuclease assay was performed by incubating 5 ul (25–150 units) of DNA polymerase with 5 ug of labelled [$^3$H]-pBR322 PCR fragment (1.6×10$^4$ cpm/ug DNA) in 100 ul of reaction buffer of 20 mM Tris.HCl pH 8.5, 5 mM MgCl$_2$, 10 mM KCl, for 1 hour at 60° C. After this time interval, 200 ul of 1:1 ratio of 50 ug/ml salmon sperm DNA with 2 mM EDTA and 20% TCA with 2% sodium pyrophosphate were added into the assay aliquots. The aliquots were put on ice for 10 min and then centrifuged at 12,000 g for 10 min. Acid-soluble radioactivity in 200 ul of the supernatant was quantitated by liquid scintillation counting. One unit of exonuclease activity was defined as the amount of enzyme that catalyzed the acid solubilization of 10 nmol of total nucleotide in 30 min at 60° C.

Utility in DNA Sequencing

EXAMPLE 1

DNA Sequencing with FY Polymerases (e.g., FY2 and FY3)

The following components were added to a microcentrifuge vial (0.5 ml) : 0.4 pmol M13 DNA (e.g., M13 mp18, 1.0 $\mu$g); 2 $\mu$l Reaction Buffer (260 mM Tris-HCl, pH 9.5 65 mM MgCl$_2$); 2 $\mu$l of labeling nucleotide mixture (1.5 $\mu$M each of dGTP, dCTP and dTTP); 0.5 $\mu$l (5 $\mu$Ci) of [a-$^{33}$P]dATP (about 2000 Ci/mmol); 1 $\mu$l –40 primer (0.5 $\mu$M; 0.5 pmol/$\mu$l 5'GTTTTCCCAGTCACGAC-3'); 2 $\mu$l of a mixture containing 4 U/$\mu$l FY polymerase and 6.6 U/ml *Thermoplasma acidophilum* inorganic pyrophophatase (32 U/$\mu$l polymerase and 53 U/ml pyrophosphatase in 20 mM Tris (pH8.5), 100 mM KCl, 0.1 mM EDTA, 1 mM DTT, 0.5% NP-40, 0.5% TWEEN-20 and 50% glycerol, diluted 8 fold in dilution buffer (10 mM Tris-HCl pH8.0, 1 mM 2-mercaptoethanol, 0.5% TWEEN-20, 0.5% NP-40)); and water to a total volume of 17.5 $\mu$l. These components (the labeling reaction) were mixed and the vial was placed in a constant-temperature water bath at 45° C. for 5 minutes.

Four vials were labeled A, C, G, and T, and filled with 4 $\mu$l of the corresponding termination mix: ddA termination mix (150 $\mu$M each dATP, dCTP, dGTP, dTTP, 1.5 $\mu$M ddATP); ddT termination mix (150 $\mu$M each dATP, dCTP, dGTP, dTTP, 1.5 $\mu$M ddTTP); ddC termination mix (150 $\mu$M each dATP, dCTP, dGTP, dTTP, 1.5 $\mu$M ddCTP); ddG termination mix (150 $\mu$M each dATP, dCTP, dGTP, dTTP, 1.5 $\mu$M ddGTP).

The labeling reaction was divided equally among the four termination vials (4 $\mu$l to each termination reaction vial), and tightly capped.

The four vials were placed in a constant-temperature water bath at 72° C. for 5 minutes. Then 4 $\mu$l of Stop Solution (95% Formamide 20 mM EDTA, 0.05% Bromophenol Blue, 0.05% Xylene Cyanol FF) added to each vial, and heated briefly to 70°–80° C. immediately prior to loading on a sequencing gel (8% acrylamide, 8.3M urea). Autoradiograms required an 18–36 hour exposure using Kodak XAR-5 film or Amersham Hyperfilm MP. High-quality sequence results with uniform band intensities were obtained. The band intensities were much more uniform than those obtained with similar protocols using Taq DNA polymerase or $\Delta$Taq DNA polymerase.

EXAMPLE 2

DNA Cycle Sequencing with FY Polymerases

The following components were added to a microcentrifuge vial (0.5 ml) which is suitable for insertion into a thermocycler machine (e.g., Perkin-Elmer DNA Thermal Cycler): 0.05 pmol or more M13 DNA (e.g., M13 mp18, 0.1 $\mu$g), or 0.1 $\mu$g double-stranded plasmid DNA (e.g., pUC19); 2 $\mu$l Reaction Buffer (260 mM Tris-HCl, pH 9.5 65 mM MgCl$_2$); 1 $\mu$l 3.0 $\mu$M dGTP; 1 $\mu$l 3.0 $\mu$M dTTP; 0.5 $\mu$l (5 $\mu$Ci) of [$\alpha$-$^{33}$P]dATP (about 2000 Ci/mmol); 1 $\mu$l –40 primer (0.5 $\mu$M; 0.5 pmol/$\mu$l 5'GTTTTCCCAGTCACGAC-3'); 2 $\mu$l of a mixture containing 4 U/$\mu$l FY polymerase and 6.6 U/ml *Thermoplasma acidophilum* inorganic pyrophophatase (32 U/$\mu$l polymerase and 53 U/ml pyrophosphatase in 20 mM Tris (pH8.5), 100 mM KCl, 0.1 mM EDTA, 1 mM DTT, 0.5% NP-40, 0.5% TWEEN-20 and 50% glycerol, diluted 8 fold in dilution buffer (10 mM Tris-HCl pH8.0, 1 mM 2-mercaptoethanol, 0.5% TWEEN-20, 0.5% NP-40)); and water to a total volume of 17.5 $\mu$l.

These components (labeling reaction mixture) were mixed and overlaid with 10 $\mu$l light mineral oil (Amersham). The vial was placed in the thermocycler and 30–100 cycles (more than 60 cycles is unnecessary) from 45° C. for 1 minute to 95° C. for 0.5 minute performed. (Temperatures can be cycled from 55°–95° C., if desired) The temperatures may be adjusted if the melting temperature of the primer/template is significantly higher or lower, but these temperatures work well for most primer-templates combinations. This step can be completed in about 3 minutes per cycle.

Four vials were labeled A, C, G, and T, and filled with 4 ml of the corresponding termination mix: ddA termination mix (150 $\mu$M each dATP, dCTP, dGTP, dTTP, 1.5 $\mu$M ddATP); ddT termination mix (150 $\mu$M each dATP, dCTP, dGTP, dTTP, 1.5 $\mu$M ddTTP); ddC termination mix (150 $\mu$M each dATP, dCTP, dGTP, dTTP, 1.5 $\mu$M ddCTP); ddG termination mix (150 $\mu$M each dATP, dCTP, dGTP, dTTP, 1.5 $\mu$M ddGTP). No additional enzyme is added to the termination vials. The enzyme carried in from the prior (labeling) step is sufficient.

The cycled labeling reaction mixture was divided equally among the four termination vials (4 $\mu$l to each termination reaction vial), and overlaid with 10 $\mu$l of light mineral oil.

The four vials were placed in the thermocycler and 30–200 cycles (more than 60 cycles is unnecessary) performed from 95° C. for 15 seconds, 55° C. for 30 seconds, and 72° C. for 120 seconds. This step was conveniently completed overnight. Other times and temperatures are also effective.

Six $\mu$l of reaction mixture was removed (avoiding oil), 3 $\mu$l of Stop Solution (95% Formamide 20 mM EDTA, 0.05% Bromophenol Blue, 0.05% Xylene Cyanol FF) added, and heated briefly to 70°–80° C. immediately prior to loading on a sequencing gel. Autoradiograms required an 18–36 hour exposure using Kodak XAR-5 film or Amersham Hyperfilm MP. High-quality sequence results with uniform band intensities were obtained. The band intensities were much more uniform than those obtained with similar protocols using Taq DNA polymerase or $\Delta$Taq DNA polymerase.

EXAMPLE 3

Sequencing with dGTP Analogs to Eliminate Compression Artifacts

For either of the sequencing methods outlined in examples 1 and 2, 7-Deaza-2'deoxy-GTP can be substituted for dGTP in the labeling and termination mixtures at exactly the same concentration as dGTP. When this substitution is made, secondary structures on the gels are greatly reduced. Similarly, 2'-deoxyinosinetriphosphate can also be substituted for dGTP but its concentration must be 10-fold higher than the corresponding concentration of dGTP. Substitution of dITP for dGTP is even more effective in eliminating compression artifacts than 7-deaza-dGTP.

EXAMPLE 4

Other Sequencing Methods Using FY Polymerases

FY polymerases have been adapted for use with many other sequencing methods, including the use of fluorescent primers and fluorescent-dideoxy-terminators for sequencing with the ABI 373A DNA sequencing instrument.

EXAMPLE 5

SDS-Polyacrylamide Gel Electrophoresis

Protein samples were run on a 14×16 mm 7.5 or 10% polyacrylamide gel. (Gels were predominantly 10% Polyacrylamide using a 14×16 mm Hoefer apparatus. Other sizes, apparatuses, and percentage gels are acceptable. Similar results can also be obtained using the Pharmacia Phast Gel system with SDS, 8–25% gradient gels. Reagent grade and ultrapure grade reagents were used.) The stacking gel consisted of 4% acrylamide (30:0.8, acrylamide: bisacrylamide), 125 mM Tris-HCl pH 6.8, 0.1% Sodium Dodecyl Sulfate (SDS). The resolving gel consisted of 7.5 or 10% acrylamide (30:0.8, acrylamide: bisacrylamide), 375 mM Tris-HCl pH 8.8, 0.1% SDS. Running Buffer consisted of 25 mM Tris, 192 mM Glycine and 0.1% SDS. 1× Sample Buffer consisted of 25 mM Tris-HCl pH 6.8, 0.25% SDS, 10% Glycerol, 0.1M Dithiothreitol, 0.1% Bromophenol Blue, and 1 mM EDTA. A ¼ volume of 5× Sample Buffer was added to each sample. Samples were heated in sample buffer to 90°–100° C. for approximately 5 minutes prior to loading. A 1.5 mm thick gel was run at 50–100 mA constant current for 1–3 hours (until bromophenol blue was close to the bottom of the gel). The gel was stained with 0.025% Coomassie Blue R250 in 50% methanol, 10% acetic acid and destained in 5% methanol, 7% acetic acid solution. A record of the gel was made by taking a photograph of the gel, by drying the gel between cellulose film sheets, or by drying the gel onto filter paper under a vacuum.

Other embodiments are within the following claims.

We claim:

1. An enzymatically active DNA polymerase comprising 561 amino acids having a tyrosine residue at an amino acid position corresponding to Taq DNA polymerase residue 667 in its dNMP binding site, wherein said polymerase lacks 5' to 3' exonuclease activity as a result of an N-terminal deletion, and wherein said polymerase is substantially identical to the DNA polymerase of *Thermus aquaticus, Thermus flavus* or *Thermus thermophilus,* and wherein said polymerase forms a single polypeptide band on an SDS polyacrylamide gel.

2. An enzymatically active DNA polymerase comprising 562 amino acids having a tyrosine residue at an amino acid position corresponding to Taq DNA polymerase residue 667 in its dNMP binding site, wherein said polymerase lacks 5' to 3' exonuclease activity as a result of an N-terminal deletion, and wherein said polymerase is substantially identical to the DNA polymerase of *Thermus aquaticus, Thermus flavus* or *Thermus thermophilus,* and wherein said polymerase forms a single polypeptide band on an SDS polyacrylamide gel.

3. The polymerase of claim 2, wherein the polymerase is FY3 (SEQ ID NO:2).

4. The polymerase of claim 1, wherein the polymerase is FY4 (SEQ ID NO:14).

5. The polymerase of claim 1 or 2 wherein the amino acid sequence of said polymerase includes less than 3 conservative amino acid changes compared to the equivalent region of one said DNA polymerase of said named Thermus species.

6. The polymerase of claim 1 or 2 wherein the amino acid sequence of said polymerase includes less than 3 additional amino acids at its N-terminus compared to the equivalent region of one said DNA polymerase of said named Thermus species.

7. The polymerase of claim 1 wherein the polymerase is FY2 (SEQ ID NO:1).

8. Purified nucleic acid encoding the DNA polymerase of any of claims 1, 7, 2, 3, or 4.

9. Method for sequencing DNA comprising the step of generating chain terminated fragments from the DNA template to be sequenced with a DNA polymerase of any of claims 1, 7, 2, 3, or 4 in the presence of at least one chain terminating agent and one or more nucleotide triphosphates, and determining the sequence of said DNA from the sizes of said fragments.

10. Kit for sequencing DNA comprising a DNA polymerase of any of claims 1, 7, 2, 3, or 4 and a pyrophosphatase.

11. The kit of claim 10 wherein said pyrophosphatase is thermostable.

12. Apparatus for DNA sequencing having a reactor comprising a DNA polymerase of any of claims 1, 7, 2, 3, or 4 and a band separator.

13. Purified nucleic acid encoding the DNA polymerase of claim 5.

14. Method for sequencing DNA comprising the step of generating chain terminated fragments from the DNA template to be sequenced with a DNA polymerase of claim 5 in the presence of at least one chain terminating agent and one or more nucleotide triphosphates, and determining the sequence of said DNA from the sizes of said fragments.

15. Kit for sequencing DNA comprising a DNA polymerase of claim 5 and a pyrophosphatase.

16. The kit of claim 15 wherein said pyrophosphatase is thermostable.

17. Apparatus for DNA sequencing having a reactor comprising a DNA polymerase of claim 5 and a band separator.

18. Purified nucleic acid encoding the DNA polymerase of claim 6.

19. Method for sequencing DNA comprising the step of generating chain terminated fragments from the DNA template to be sequenced with a DNA polymerase of claim 6 in the presence of at least one chain terminating agent and one or more nucleotide triphosphates, and determining the sequence of said DNA from the sizes of said fragments.

20. Kit for sequencing DNA comprising a DNA polymerase of claim 6 and a pyrophosphatase.

21. The kit of claim 20 wherein said pyrophosphatase is thermostable.

22. Apparatus for DNA sequencing having a reactor comprising a DNA polymerase of claim 6 and a band separator.

* * * * *